US007983887B2

(12) United States Patent
Agarwal

(10) Patent No.: US 7,983,887 B2
(45) Date of Patent: Jul. 19, 2011

(54) FAST COMPUTATIONAL METHODS FOR PREDICTING PROTEIN STRUCTURE FROM PRIMARY AMINO ACID SEQUENCE

(75) Inventor: Pratul Kumar Agarwal, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 419 days.

(21) Appl. No.: 11/796,418

(22) Filed: Apr. 27, 2007

(65) Prior Publication Data

US 2008/0270094 A1 Oct. 30, 2008

(51) Int. Cl.
*G06G 7/48* (2006.01)
(52) U.S. Cl. ............................................ 703/11; 702/19
(58) Field of Classification Search ............................ None
See application file for complete search history.

(56) References Cited

U.S. PATENT DOCUMENTS

| | | | |
|---|---|---|---|
| 4,853,871 A | 8/1989 | Pantoliano |
| 5,241,470 A | 8/1993 | Lee |
| 5,260,882 A | 11/1993 | Blanco |
| 5,265,030 A | 11/1993 | Skolnick |
| 5,436,850 A | 7/1995 | Eisenberg |
| 5,553,004 A | 9/1996 | Gronbech-Jensen |
| 5,557,535 A | 9/1996 | Srinivasan |
| 5,579,250 A | 11/1996 | Balaji |
| 5,600,571 A | 2/1997 | Friesner |
| 5,680,319 A | 10/1997 | Rose |
| 5,740,072 A | 4/1998 | Still |
| 5,784,294 A | 7/1998 | Platt |
| 5,842,151 A | 11/1998 | Noguchi |
| 5,878,373 A | 3/1999 | Cohen |
| 5,884,230 A | 3/1999 | Srinivasan |
| 6,178,384 B1 | 1/2001 | Kolossvary |
| 6,512,981 B1 | 1/2003 | Eisenberg |
| 6,797,482 B2 | 9/2004 | Woods |
| 6,832,162 B2 | 12/2004 | Floudas |
| 6,882,939 B2 | 4/2005 | Homans |
| 6,968,275 B1 | 11/2005 | Shackleford |
| 2002/0137118 A1 | 9/2002 | Inouye |
| 2002/0150906 A1 | 10/2002 | Debe |
| 2003/0130797 A1 | 7/2003 | Skolnick |
| 2003/0135331 A1 | 7/2003 | Hogue |
| 2003/0158672 A1 | 8/2003 | Ramnarayan |
| 2004/0083061 A1 | 4/2004 | Hannah |
| 2004/0096897 A1 | 5/2004 | Zhou |
| 2004/0215400 A1 | 10/2004 | Slovic |
| 2004/0219601 A1 | 11/2004 | Xu |
| 2005/0009735 A1 | 1/2005 | Kim |
| 2005/0053999 A1 | 3/2005 | Gough |

(Continued)

OTHER PUBLICATIONS

Higo et al. Protein Engineering vol. 10 No. 4 pp. 373-380, 1997.*

(Continued)

*Primary Examiner* — Michael Borin
(74) *Attorney, Agent, or Firm* — Scully, Scott, Murphy & Presser, P.C.

(57) ABSTRACT

The present invention provides a method utilizing primary amino acid sequence of a protein, energy minimization, molecular dynamics and protein vibrational modes to predict three-dimensional structure of a protein. The present invention also determines possible intermediates in the protein folding pathway. The present invention has important applications to the design of novel drugs as well as protein engineering. The present invention predicts the three-dimensional structure of a protein independent of size of the protein, overcoming a significant limitation in the prior art.

19 Claims, 12 Drawing Sheets
(5 of 12 Drawing Sheet(s) Filed in Color)

U.S. PATENT DOCUMENTS

| | | |
|---|---|---|
| 2005/0069954 A1 | 3/2005 | Sakai |
| 2005/0090991 A1 | 4/2005 | Dawson |
| 2005/0112683 A1 | 5/2005 | Reiner |
| 2006/0019318 A1 | 1/2006 | Lingappa |

OTHER PUBLICATIONS

Go et al. Proc. Nati Acad. Sci. USA, vol. 80, pp. 3696-3700, Jun. 1983.*

Krim et al. Faraday Discuss., 1994,99,181-197.*

Tasumi et al. Biopolymers, vol. 21, 711-714, 1982.*

Moritsugu et al. Phys. Chem. B, 2005, 109 (24), pp. 12182-12194.*

Agarwal, Pratul K., "Enzymes: An Integrated View of Structure, Dynamics and Function", *Microbial Cell Factories*, vol. 5, No. 2, pp. 1-12 (2006).

Agarwal et al., "Protein Dynamics and Enzymatic Catalysis: Investigating the Peptidyl-Prolyl Cis-Trans Isomerization Activity of Cyclophilin A", *Biochemistry*, vol. 43, No. 33, pp. 10605-10618 (2004).

Carnevali et al., "Fast Protein Structure Prediction Using Monte Carlo Simulations with Modal Moves", *J. Am. Chem. Soc.*, vol. 125, pp. 14244-14245 (2003).

Chen et al., "A Directed Essential Dynamics Simulation of Peptide Folding", *Biophysical Journal*, vol. 88, pp. 3276-3285 (2005).

Delarue et al., "On the Use of Low-Frequency Normal Modes to Enforce Collective Movements in Refining Macromolecular Structural Models", *Proceedings of the National Academy of Sciences of the United States of America*, vol. 101, pp. 6957-6962 (2004).

Eisenmesser et al., "Enzyme Dynamics During Catalysis", *Science*, vol. 295, pp. 1520-1523 (2002).

Zhang et al., "Molecular Dynamics Simulations of Peptides and Proteins with Amplified Collective Motions", *Biophysical Journal*, vol. 84, pp. 3583-3593 (2003).

Zheng et al., "Modeling Protein Conformational Changes by Iterative Fitting of Distance Constraints Using Reoriented Normal Modes", *Biophysical Journal*, vol. 90, pp. 4327-4336 (2006).

Zheng et al., "Low-Frequency Normal Modes That Describe Allosteric Transitions in Biological Nanomachines are Robust to Sequence Variations", *Proceedings of the National Academy of Sciences of the United States of America*, vol. 103, pp. 7664-7669 (2006).

* cited by examiner (a)

(b)

(a) Native Structure solved experimentally using NMR (PDB code: 1VII)

(b) Prediction of 3-D structure and mechanism of protein folding using invented technology (a)

(b)

(a) Ubiquitin: Native Structure solved experimentally (PDB code: 1UBQ)

(b) Using displacement along protein vibrational modes (force-field parm98)

(c) Same as (b) except force-field parm03 and implicit solvent conditions (a) Dihydrofolate Reductase: Native Structure solved experimentally using X-ray (PDB code: 1RX2)

(b) Investigating 3-D structure and mechanism of protein folding using invented technology (a) Cyclophilin A: Native Structure solved experimentally using X-ray (PDB code: 1RMH)

(b) Investigating 3-D structure and mechanism of protein folding using invented technology

FAST COMPUTATIONAL METHODS FOR PREDICTING PROTEIN STRUCTURE FROM PRIMARY AMINO ACID SEQUENCE

The United States Government has rights in this invention pursuant to contract no. DE-AC05-00OR22725 between the United States Department of Energy and UT-Battelle, LLC.

FIELD OF INVENTION

The invention relates to the prediction of the three-dimensional structure of a protein and the mechanism of protein folding. More specifically the invention relates to the prediction and/or refinement of the three dimensional structure of a protein from its primary amino acid sequence, based on fast searching of the conformational space of a protein. The invention also relates to obtaining a set of intermediates from alternate pathways in order to determine the mechanism of protein folding.

BACKGROUND OF THE INVENTION

The 3-dimensional structure of a folded and functioning protein is determined by the primary sequence of amino acids. This protein structure is commonly referred to as the native state and is the protein conformation which allows the protein to perform its designated function. This native state is considered to be deterministic, as the given primary sequence of a protein has a unique 3-dimensional structure in the native state (under ambient conditions). A better understanding of proteins in their natural environment is based on recent investigations that have lead to a slightly refined definition of the native state, defining it as an average structure of an ensemble of structures that deviate within small limits (N. Furnham et al., Nature Structure & Molecular Biology (2006), 13, 184-185, M. A. DePristo et al., Structure (2004) 12, 831-838). Other definitions of native state suggest the most populated state in an ensemble of similar structures (M. A. DePristo et al., Structure (2004) 12, 831-838). An algorithm to predict the folded structure (hereinafter called the native state) of a protein has immense potential applications, including drug design for protein targets where the structure is not available from experimental studies or is expensive to produce through experimental investigations. Further, the fundamental understanding of the mechanism of protein folding is very poorly understood. A better understanding of protein folding mechanisms has broad implications in understanding diseases, such as Alzheimer's and Parkinson's diseases, which result from misfolded or disordered proteins.

Numerous approaches have been proposed to predict the 3-dimensional native structure of the protein based on the primary sequence, which have been surveyed in detail elsewhere (C. D. Snow et al., Ann. Rev. Biophysics Biomolecular Structure (2005), 34:43-69, B. Kuhlman et al., Current Opinion in Structural Biol. Feb. 14, 2004 (1):89-95). Some of these approaches are known as "ab-initio", as they require only the knowledge of primary sequence. Other approaches use information from experimentally solved structures in some form of a database or a reference set. The later approach has made significant progress in the recent years; however, it has limited success in cases where relevant protein folds are not available (i.e. the database is limited, for example in the case of membrane proteins). Further, these methods are not able to discern the mechanism of protein folding.

In most ab-initio approaches, some form of atomistic modeling of the protein (or a reduced model of protein structure—for example only considering the protein backbone or including hydrogen atoms into heavy atoms) is used, which is commonly referred to as molecular mechanics. The challenge of folding a protein, through computer modeling and simulations using molecular mechanics, lies in finding the global minimum of the protein conformational energy landscape. There is sufficient experimental and theoretical evidence that the folded structure, or the native state, corresponds to a region close to the global energy minimum. A popular understanding of the protein conformational energy landscape describes it as a "folding funnel" (K A Dill et al., Nature Structural Biol., 1997, 4(1):10-9). The bottom of this funnel represents the native state with lowest energy conformation, and the surface of this funnel is not smooth and consists of local energy minima and maxima (see FIG. 1). Further the starting points with different extended conformations start from the different top portions of the funnel but eventually reach the same native state following alternate pathways.

In the molecular mechanics approach, the conformational energy is described as a mathematical function of geometrical variables inside the protein. The underlying mathematical function and variables are referred to as the potential function and the degrees of freedom of a protein, respectively. A typical potential function is shown in Equation 1, where the first term corresponds to the bond stretching term, the second term corresponds to the angle bending term, the third term corresponds to the angle torsion (dihedral) term. The last term is commonly referred as the non-bonded term, representing van der Waals and electrostatic energy components respectively.

$$V(r^N) = \sum_{bonds} K_l(l-l_{eq})^2 + \sum_{angles} K_\theta(\theta-\theta_{eq})^2 + \sum_{torsions} \frac{V_n}{2}(1+\cos[n\phi-\gamma]) + \sum_{i=1}^{N}\sum_{j=i+1}^{N}\left(\left[\frac{A_{ij}}{r_{ij}^{12}} - \frac{B_{ij}}{r_{ij}^{6}}\right] + \frac{q_i q_j}{\varepsilon r_{ij}}\right) \quad \text{(Eq. 1)}$$

A protein with N atoms has 3N−6 internal degrees of freedom; in other words, the protein conformational space has 3N−6 dimensions. If only ten points are used to sample each dimension (in an oversimplified description of the protein conformational space), the total number of points to be sampled are $10^{3N-6}$. The size of a protein conformational energy space, therefore, increases very rapidly with the number of atoms in the protein. Mathematically, the conformational energy function is highly multi-dimensional (if each degree of freedom defines one dimension). For a small protein (with about 100 amino acid residues) N is typically between 1,000 and 2,000. The conformational space for a biologically relevant protein is extremely large with total number of points to be evaluated are $M^{3N-6}$, if it is assumed that M points on average are evaluated per dimension. Therefore, using such equations, it is impossible to exhaustively explore the complete conformational space even for a small protein in a reasonable time-frame. It is known that a native protein can fold in milliseconds, however, sampling of such a large number of points in a protein would take several millions years. This is what has been mentioned as Levinthal's Paradox in literature (Levinthal, C., Journal de Chimie Physique et de Physico-Chimie Biologique 1968, 65, 44).

In nature, proteins have been known to fold quickly from an extended or misfolded state to the native state. It is known that a native protein can fold in milliseconds, however, sampling a large number of points (as discussed above) even by a protein would take several millions years. This is what has been mentioned as Levinthal's Paradox in literature (Levinthal, C., Journal de Chimie Physique et de Physico-Chimie Biologique 1968, 65, 44). Therefore, it has been widely suggested that a protein goes from extended conformations to the native state through a process which is referred to as the mechanism of protein folding. During this process the extended conformation which is higher in energy, follows pathways consisting of local minima and local maxima, to eventually reach the global energy minima that corresponds to the native state (see FIG. 1). In most cases it has been shown that the information required to achieve the native state is present in the protein sequence. In some cases molecules known as chaperones assist the proteins to reach their native state. Experimentally, it has been difficult to obtain detailed information about the mechanism of protein folding because the intermediate states are transient (C. R. Matthews et al., Ann. Rev. Biochem. (1992), 62: 653-83, A. C. Apetri et al., J. Am. Chem. Society (2006);128(35):11673-8).

Some previous investigations have explored displacement of protein structure along normal modes to predict folded protein structure. However, these studies suffer from serious limitations, preventing them from predicting three-dimensional structure of proteins. Further, these studies have not reported any information on the mechanism of protein folding. First, they have only explored the use of fast vibrations on femtosecond time-scale using peptides of 15-amino acid residues (C. Chen et al., Biophysical J., (2005), 88: 3276-3285). Note in the cited study the modes were computed using principal component analysis on very short molecular dynamics trajectories, and did not explore the more important vibrational modes from longer time-scales. Further, past studies have not proposed the use of protein vibrational modes that are computed using quasi harmonic analysis based on a set of structures from different areas of the protein conformational space, which allows overcoming large energy barriers between different conformations. More importantly, past studies they have only explored very small model size (15-20 amino acid residues) peptides and have not shown results from actual proteins (Z. Zhang et al., Biophysical J., (2003) 84: 3583-3593 and P. Carnevali et al., Am. Chem. Soc. (2003) 125 (47): 2003 14245).

Therefore, there is considerable interest in and need for a methodology that can efficiently predict the three-dimensional structure of a protein from its primary amino acid sequence and the mechanism of protein folding.

SUMMARY OF THE INVENTION

This invention provides a method for predicting and/or refining the three-dimensional structure of a protein from its primary amino acid sequence and determining the mechanism or folding pathway of a protein. This is achieved by rapidly exploring the conformational space of a protein, which represents all possible conformations for a protein with a given primary sequence, based on the use of protein vibrational modes. The fast search is made possible by dividing the conformational space and using several protein vibrational modes as search dimensions to explore the conformational space (FIG. 2). The use of protein vibrational modes to search the conformational space is based on the understanding that internal protein dynamics play a role in overcoming energy barriers that exist in the protein folding pathway (P. K. Agarwal et al., J. Am. Chem. Soc. (2005) 127, 15248-15246, P. K. Agarwal et al., Biochemistry (2004) 43, 10605-10618, P. K. Agarwal et al., Proteins: Structure Function and Bioinformatics (2004) 56, 449-463). Protein dynamics refers to the internal motions of proteins in solution which occur at different time-scales, ranging from femtoseconds to seconds. Vibrational modes describe these motions by describing the magnitude of motion and velocities of each atom in the protein at a given time-scale.

The present invention initially defines an extended conformation of the protein or starts from a partially folded structure obtained from other sources. The coordinates of the initial extended conformation can be assigned based on the primary amino acid sequence or can be based on information determined through experimental techniques such as X-ray crystallography or NMR (or other experimental and computational techniques). The five stages in the typical implementation of the method are exemplified in FIG. 3.

Stage 1: Involves relaxation of the protein conformation (extended or partially folded) by using a method such as energy minimization (EM), which relieves local strains in the conformation.

Stage 2: The second step involves generation of a time-trajectory using the molecular dynamics (MD), the result of which is a set of coordinates and velocities for each atom in the protein taken at equal time or sampling intervals.

Stage 3: The conformations sampled in Stage 2 are used to compute protein vibrational modes.

Stage 4: The information from multiple vibrational modes is then used in this stage to displace the initial conformation along these different vibrational modes (several modes are explored simultaneously). In the case of displacement of structures along protein vibrational modes, it will either result in a conformation in a higher energy state (over-stretched bonds, close atom-atom interactions) that will return to the initial conformation upon energy minimization, or will overcome a local energy barrier, adopting a new conformation in a lower energy state upon energy minimization. In an alternative embodiment, rather than displace the initial conformation along the vibrational modes, kinetic energy can be added to the vibrational modes by scaling velocities proportional to the atomic displacements indicated by the protein vibrational mode. This additional kinetic energy allows the conformation to overcome local energy barriers permitting the conformation to approach and reach the global minima of the native fold.

Stage 5: In the fifth step, starting from the structures prepared in step 4 searches for new conformations are made in multiple directions (by use of simultaneous runs in several different directions based on the vibrational modes calculated in step 3). During this step the protein structure is relaxed through use of energy minimization and/or molecular dynamics. Finally at the end of each cycle, the results from different independent searched performed in Stage 5 are compared and the conformation with the lowest potential energy is then used as the starting conformation and the process is repeated. The process is repeated until the native state or fold is determined. This can be accomplished by comparing the predicted structure to known structural information of the protein (at lower resolution or partial structure of proteins), if available. In most cases this information will not be available so other criteria must be used. Typically several criteria have been developed to evaluate the energetic or structural progress of the protein conformation toward the native state. These criteria are referred broadly as "scoring functions". These scoring functions include monitoring, through computing, a number of the protein's biophysical properties including the energy, radius of gyration and surface area (polar and non-polar) and others. When the native state is reached, further displacement of the conformation will fail to produce additional changes in structure, potential energy and surface area. Likewise the radius of gyration, which is large for extended conformation, continues to decrease as protein progresses toward the native state. Around the native state the radius of gyration for a globular protein typically stabilizes and does not decrease significantly beyond a certain value. Based on statistical analysis of a large group of proteins, previous studies have derived a relationship between the number of protein residues and the radius of gyration of a protein in the native state. This empirical relationship is given by the formula radius of gyration=$0.359*N^{3/5}+7.257$, where N is number of protein residues. This formula has been derived by fitting to a variety of protein structures in the protein data bank (PDB). (For more details see P. Narang et al., Physical Chemistry Chemical Physics (2005) 7, 2364-2375).

Further, the values for potential energy, surface area and radius of gyration can be compared to the known values of related proteins. In cases where related structures are not available for comparison then the convergence is tested by evaluating the changes in potential energy, surface area and radius of gyration. Changes in potential energy are evaluated first for approximately 50 (in case of smaller proteins) to approximately 500 (in case of larger proteins) cycles (or about 3-25% of the protein vibrational modes), followed by evaluation of changes in the surface area and the radius of gyration. In the extended state the system energy provides a quick method for convergence, however, nearing the native state, surface area and radius of gyration provide more reliable predictions.

A criterion for reaching native state, in one embodiment, is that the potential energy does not decrease by more than a value within the range of 0.1 kcal/mol to 1 kcal/mol in the last 100 cycles, including but not limited to the following values: 0.2, 0.3, 0.4, 0.5, 0.6, 0.7, 0.8, or 0.9 kcal/mol. In another embodiment, a criterion for reaching native state is that the potential energy does not decrease by more than 1 kcal/mol in the last 100 cycles. In yet another embodiment, a criterion for reaching native state is that the potential energy does not decrease by more than 0.1 kcal/mol in the last 100 cycles.

Similarly, a criterion for reaching the native state is that the radius of gyration or the surface area does not decrease by more than a value within the range of 0.01% to 2.0% in last 100 cycles, including but not limited to the following values: 0.025%, 0.05%, 0.075%, 0.1%, 0.25%, 0.5%, 0.75%, 1%, 1.25%, 1.5%, or 1.75%. Similarly, another criterion for reaching the native state is that the radius of gyration or surface area does not decrease by more than 1% in last 100 cycles.

Note, the lack of a computational prediction that completely agrees with the structure available in the protein data bank, can be attributed to problems arising from calculating molecular mechanics potentials (force-fields). This problem is a well known and documented fact within the art (M. J. Hsieh et al., Proteins, 56 (2004) 475-486; A. Okur et al., J. Comput Chem, 24 (2003) 21-31). The type of scoring functions used have a direct impact on the prediction of the native state, however, as the quality of scoring functions is improved, the prediction of the native state also improves. Further steps that can be taken to improve the accuracy of prediction include but are not limited to: an iterative scheme for improving the force-field based on the pool of available protein structures in the protein data bank and other sources (M. J. Hsieh et al., Proteins, 56 (2004) 475-486; A. Okur et al., J. Comput. Chem., 24 (2003) 21-31). However more importantly new criteria for the evaluation of energy comparison based on more accurate evaluation using semi-empirical or quantum methods will eventually remove this limitation (K. Raha, et al., J. Med. Chem. 2005, 48, 4558-4575).

This invented method has applications to drug discovery and design. The need to predict three dimensional structure of a protein in order to design more effective drug small molecules is well documented (N. Vaidehi, et al., Proc. Natl. Acad. Sci. USA (2002) 99, 12622-12627). While a number of protein structures have been resolved experimentally, there remain a number of therapeutically attractive targets, such as many G-coupled protein receptors, whose structures have not been determined. G-coupled protein receptors belong to a class of proteins known as membrane proteins. Obtaining the structure of membrane proteins, either from experiments or computations, has been difficult. Experimentally these proteins are hard to crystallize and also their structure in aqueous solution is very different than their native environment. Computationally methods which rely on using information from similar proteins do not perform well, as not enough structures are available for membrane proteins. The present invention is suitable for such proteins as it can allow simulating the protein folding in non-aqueous environments as well. The protein can be simulated in non-polar solvent such as lipid molecules to provide structural predictions for membrane proteins. Non-polar solvents can be explicitly modeled similar to the way simulation of water is performed. The process is similar to the case of polar solvent, in which the modeled protein is surrounded by a box of non-polar solvent. The parameters for non-polar solvent can be derived as recommended by the MD force-field in use for the protein. Note that since very limited information of protein structure in non-polar environments is available in the protein data bank (or other databases of solvent protein structure), methods that rely on this information to predict protein structure, have had limited success. The present invention does not require this information as input. Therefore this method is useful in determining the three-dimensional structure of proteins that would otherwise be experimentally difficult or expensive to obtain.

In the process of predicting three-dimensional structure of proteins, the current method can determine the mechanism or pathway by which the protein arrives at its native fold. At the end of each cycle of the above method, a conformation representing the lowest energy state is determined among multiple displaced conformations. Experimental and theoretical evidence has indicated that intermediates in the protein folding pathway exist in local energy minima separated by local energy barriers (K A Dill et al., Nature Structural Biol., 1997, 4(1):10-9). Experimentally, intermediates are hard to isolate given their highly transient properties. In contrast the current method can identify the coordinates of all possible intermediate conformations in a folding pathway. This information can then be used to identify nucleation regions, areas within the protein where higher order secondary and tertiary structure first form. This information is used to determine the energy associated with the motion of residues within this nucleation region and therefore the energy barriers that exist in reaching that conformation. The method also provides coordinate information regarding spatial arrangements between neighboring residues and whether certain residue-residue interactions, like hydrogen-bonding, hydrophobic-hydrophobic interactions or disulfide bonds, play a critical role in the formation of certain higher order structures.

The mechanism of protein folding is an essential biophysical process that impacts the rate of protein production in the cell, therefore, understanding of this process is vital for understanding many aspects the biochemical processes. Further, understanding the mechanism of protein folding also has implications for understanding and curing diseases caused by the misfolding of proteins such as Alzheimer's and Creutzfeldt-Jakob disease (Dobson C. M., Nature (2003), 426, 884-890). Furthermore, understanding the mechanism of protein folding is useful in protein engineering. The ability to identify critical amino acid residues in nucleation regions will directly lead to modifications of these amino acids that can enhance the kinetics of protein folding and also allow for modifications that produce more stable proteins. Further, the present invention can be employed to analyze specific regions in proteins, such as critical sites for binding to a receptor, and catalytic sites in enzymes. The present invention is useful in designing new proteins and finding cures for diseases that are a result of misfolded proteins. The understanding of the underlying mechanism of protein folding including the vital information of the nucleation points and the role of critical residues during the mechanism is important in designing new proteins. New proteins can be designed by modifying the critical residues in the identified nucleation regions.

Drug molecules with the capability of stabilizing the disordered nucleation region will help in preventing misfolded or possibly disordered proteins. The present invention allows rapid and efficient investigation of protein folding of existing proteins as well as detailed computational simulations of a variety of "theoretical proteins" to select proteins with desired functionalities. The present invention provides significant increases in the speed of predicting the three-dimensional structure of a protein from the primary amino acid sequence.

It is an object of the present invention to provide a method for predicting the three-dimensional structure of a protein from the primary amino acid sequence using an iterative method involving energy minimization, molecular dynamics, calculation of the protein vibrational modes, and searching the protein conformational space utilizing vibrational modes as the search dimension.

It is a further object of the invention to further refine and complete partial three-dimensional structure information (partially folded structure) determined from other computational or experimental techniques using the protein three-dimensional structure prediction method of the present invention.

It is a further object of the invention to provide a method of determining the mechanism of protein folding for a protein from its primary amino acid sequence using an iterative method involving energy minimization, molecular dynamics, calculation of the protein vibrational modes, and searching of the protein conformational space utilizing vibrational modes to identify intermediate conformations found in local energy minima.

These and other objects, features and advantages of the present invention will become apparent after a review of the following detailed description of the disclosed embodiments and claims.

BRIEF DESCRIPTION OF THE DRAWINGS

The patent or application file contains at least one drawing executed in color. Copies of this patent or patent application publication with color drawings will be provided by the Office upon request and payment of the necessary fees.

DETAILED DESCRIPTION OF THE INVENTION

Definitions

Figure 1:
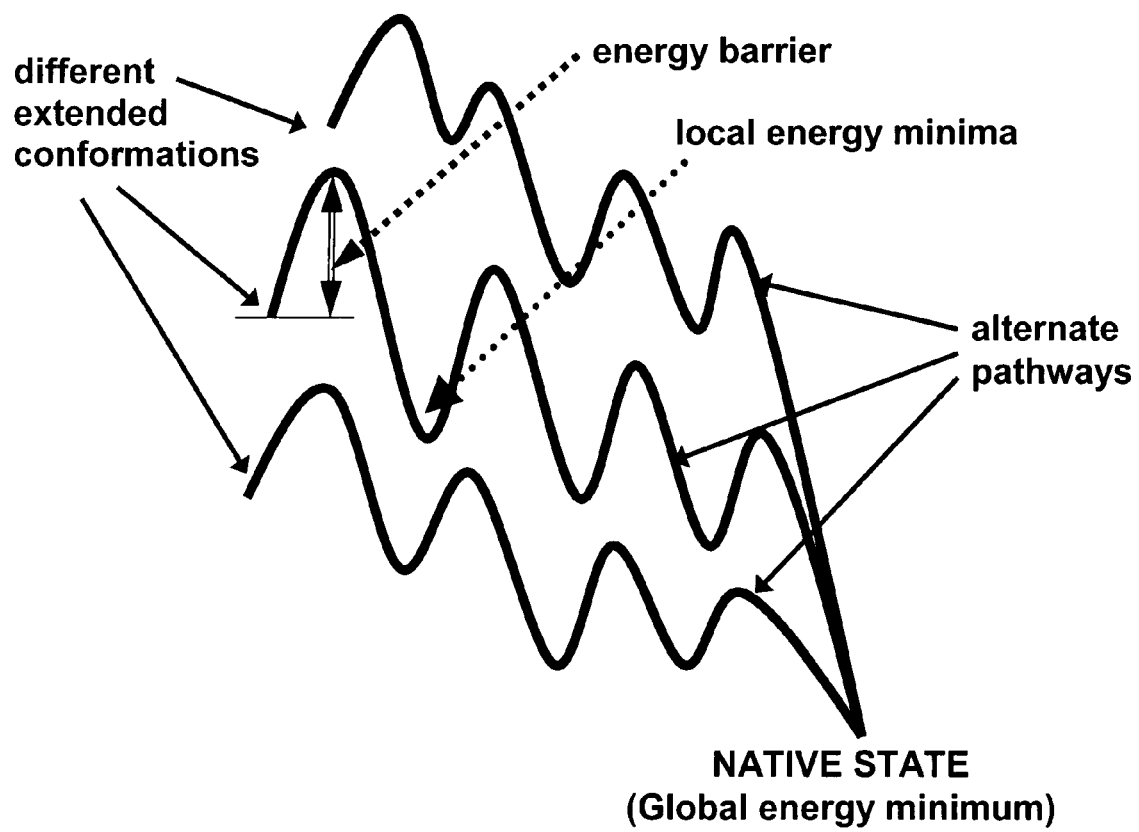
FIG. 1 is a schematic drawing demonstrating the pathway of protein folding, described in terms of intermediates and energy barriers which separate these intermediates. Starting from different extended conformations and following multiple pathways the protein conformation reaches the native state. The native state has the lowest conformational energy, which is referred as the global energy minimum. The regions of high energy are referred as energy barriers while the regions with lower energy are energy minima. An energy minimum, except for global energy minimum, is referred to as a local energy minimum. The collection of structures at various points along the different paths describes the protein folding mechanism.

The terms native state, native fold and native conformation as used in this specification refer to the 3-dimensional structure of a folded and functioning protein as determined by its primary amino acid sequence.

The term conformational space refers to a collection of all possible 3-dimensional conformations a given protein with a given primary amino acid sequence may take. The protein conformations in a conformational space may be defined by the Cartesian coordinates (x, y, z) or by the internal coordinates (bond lengths, bond angles, torsion angles) of each atom in the protein.

The terms conformational energy surface and conformational energy landscape refer to the energies associated with the conformations in the conformational space of the protein.

The term intermediate states in the protein folding pathway refer to the local minimum energy structures that are separate by higher energy regions. The high energy regions are referred to as energy barriers. A collection of intermediate structures from alternative pathways going from an unfolded protein to a native state provides information about the mechanism of protein folding.

Overview

The challenge of folding a protein, through computer modeling lies in finding the global minimum of the protein conformational energy landscape. In order to reach the global minima the protein progresses through a series of intermediate conformations, subsequent intermediates are lower in energy than the preceding conformation, until the native fold at the global minima is reached.

The present invention initially defines an extended conformation of the protein, or starts from a partially folded structure obtained from other sources. The coordinates of the initial extended conformation can be assigned based on the primary amino acid sequence or can be based on information determined through experimental techniques such as X-ray crystallography or NMR (or other experimental and computational techniques). The five stages in the typical implementation of the method are exemplified in FIG. 3.

Stage 1: Involves relaxation of the protein conformation by using a method such as energy minimization (EM), which relieves local strains in the conformation.

Stage 2: The second step involves generation of a time-trajectory using the molecular dynamics (MD), the result of which is a set of coordinates and velocities for each atom in the protein taken at equal time or sampling intervals.

Stage 3: The conformations sampled in Stage 2 are used to compute protein vibrational modes.

Stage 4: The information from multiple vibrational modes is then used in this stage to displace the initial conformation along these different vibrational modes (several modes are explored simultaneously). In the case of displacement of structures along protein vibrational modes, it will either result in a conformation in a higher energy state (overstretched bonds, close atom-atom interactions) that will return to the initial conformation upon energy minimization, or will overcome a local energy barrier, adopting a new conformation in a lower energy state upon energy minimization. In an alternative embodiment, rather than displace the initial conformation along the vibrational modes, kinetic energy can be added to the protein vibrational modes by scaling velocities proportional to the atomic displacements indicated by the protein vibrational mode. This additional kinetic energy allows the conformation to overcome local energy barriers permitting the conformation to approach and reach the global minima of the native fold.

Stage 5: In the fifth step, starting from the structures prepared in step 4, searches for new conformations are made in multiple directions (by use of simultaneous runs in several different directions based on the vibrational modes calculated in step 3). During this step the protein structure is relaxed through use of energy minimization and/or molecular dynamics. Finally at the end of each cycle, the results from different independent searched performed in Stage 5 are compared and the conformation with the lowest potential energy is then used as the starting conformation and the process is repeated. The process is repeated until the native state or fold is determined. This can be accomplished by comparing the predicted structure to known structural information of the protein (at lower resolution or partial structure of proteins), if available. In most cases this information will not be available so other criteria must be used. Typically several criteria have been developed to evaluate the energetic or structural progress of the protein conformation toward the native state. These criteria are referred broadly as "scoring functions". These scoring functions include monitoring, through computing, a number of the protein's biophysical properties including the energy, radius of gyration and surface area (polar and non-polar) and others. When the native state is reached, further displacement of the conformation will fail to produce additional changes in structure, potential energy and surface area. Likewise the radius of gyration, which is large for extended conformation, continues to decrease as protein progresses toward the native state. Around the native state the radius of gyration for a globular protein typically stabilizes and does not decrease significantly beyond a certain value. As indicated by statistical analysis of a large group of proteins, previous studies have derived a relationship between the number of protein residues and the radius of gyration of a protein in the native state. This empirical relationship is given by the formula radius of gyration=$0.359*N^{3/5}+7.257$, where N is number of protein residues. This formula has been derived by fitting to a variety of protein structures in the protein data bank (PDB). (For more details see P. Narang et al., Physical Chemistry Chemical Physics (2005) 7, 2364-2375).

Further, the values for potential energy, surface area and radius of gyration can be compared to the known values of related proteins. In cases where related structures are not available for comparison then the convergence is tested by evaluating the changes in potential energy, surface area and radius of gyration. Changes in potential energy are evaluated first for approximately 50 (in case of smaller proteins) to approximately 500 (in case of larger proteins) cycles (or about 3-25% of the protein vibrational modes), followed by evaluation of changes in the surface area and the radius of gyration. In the extended state the system energy provides a quick method for convergence, however, nearing the native state, surface area and radius of gyration provide more reliable predictions. Note, during the initial steps while evaluating the changes in potential energy about 3-5% of the protein vibrational modes are explored simultaneously. An increased number of modes are explored as described below for final convergence.

In one embodiment, a criterion for reaching the native state is that the potential energy does not decrease by more than a value within the range of 0.1 kcal/mol to 1 kcal/mol in the last 100 cycles, including but not limited to the following values: 0.2, 0.3, 0.4, 0.5, 0.6, 0.7, 0.8, or 0.9 kcal/mol. In one embodiment, a criterion for reaching native state is that the potential energy does not decrease by more than 1 kcal/mol in the last 100 cycles. In one embodiment, a criterion for reaching native state is that the potential energy does not decrease by more than 0.1 kcal/mol in the last 100 cycles.

Similarly, a criterion for reaching the native state is that the radius of gyration or the surface area does not decrease by more than a value within the range of 0.01% to 2.0% in last 100 cycles, including but not limited to the following values: 0.025%, 0.05%, 0.075%, 0.1%, 0.25%, 0.5%, 0.75%, 1%, 1.25%, 1.5%, or 1.75%. Similarly, another criterion for reaching the native state is that the radius of gyration or surface area does not decrease by more than 1% in last 100 cycles.

Figure 3:
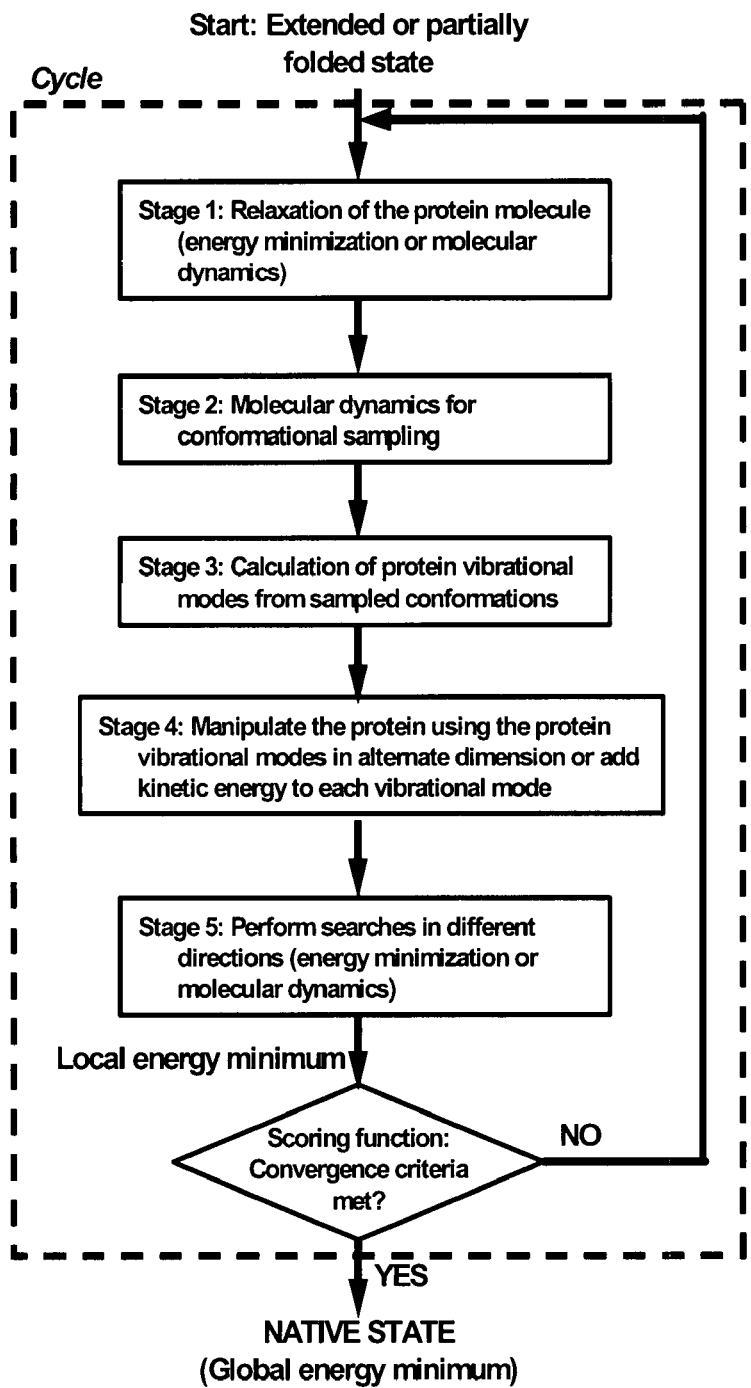
FIG. 3 shows a flow chart of the steps involved in predicting protein structure Using more than one embodiment of the present invention. Five stages as described for each cycle. Starting from the extended or partially folded structure the 5 stages are repeated iteratively. At the end of each cycle the energy (or other relevant quantity) is evaluated using a scoring function. If the scoring function indicates convergence then the native structure has been reached, if the scoring function does not indicate convergence then the cycle is repeated again until convergence is reached. The convergence criteria used is when the energy for the system does not decrease by more than 0.1 kcal/mol in last 100 steps or radius of gyration/surface area does not decrease by more than 1% in the last 100 steps.

The iterations of the five process steps shown in FIG. 3 are repeated. The energy of the system as well as the overall shape of the system starts to change quickly in the beginning. However, when approaching the native state the energy convergence becomes slower. In one embodiment, all the protein vibrational modes are explored and if the energy does not decrease at all then the native state is reached. However, if the number of protein vibrational modes is very large, this approach may not be possible with some computing systems due to the large amount of computational time required. In another embodiment, a limited number of protein vibrational modes is tested, for example 500 to 1000 modes for large proteins, and if neither a significant decrease in potential energy (for example more than 1 kcal/mol) or a large change in structure with small change is energy is observed then the system is fairly close to the energy minimum (FIG. 1).

In the beginning of the process, a limited number of vibrational modes are explored. To test for full convergence, about 3-25% of the modes are explored, depending upon the level of accuracy desired. It is to be understood that any percentage of the modes within the range of 3 to 25% may be explored. In situations where a lower degree of accuracy is acceptable, no more than about 3-10% of the vibrational modes are explored. In situations when high accuracy is desired then about 20-25% of the vibrational modes can be explored. The native secondary structure elements start to form within the first 50 cycles. In further cycles alternate secondary structures are explored as well. The first 20 modes have a significant influence on the overall shape of the protein.

Note that if a small change in energy is encountered with a large change in structure, the current conformation may be in a local minima and the new conformation should be explored further by calculating the typical number of modes, for example 10 to 20 modes.

The invented technology shows rapid progress from extended conformation toward the native structure. As a general observation, the native secondary structural elements start to form within the first 50 cycles. In further cycles alternate secondary structures are explored as well. The first 20 modes have a significant influence on the overall shape of the protein. In order to progress through these intermediate conformations, energy barriers between each intermediate must be overcome (FIG. 1). In the naturally existing systems, the energy needed to overcome these barriers is transferred to a protein from the surrounding solvent and results in increased motion of the atoms in the protein (P. K. Agarwal et al., J. Am. Chem. Soc. (2005) 127, 15248-15246). The larger barriers present between the intermediate states require more energy from the surrounding solvent, which corresponds to protein motions, or the protein vibrational modes, that span larger regions of the protein structure. As discussed in detail below, the larger motions correspond to longer time-scale of these internal atomic motions in the protein, which also means that the low frequency protein vibrational modes span a larger part of the protein structure. Manipulation of the coordinates and/or supplying energy to overcome the corresponding energy barrier allows sampling areas of conformational space that correspond to changes in the larger parts of the protein structure (which typically corresponds to distant areas of conformational space or important intermediates in the mechanism of protein folding).

Figure 2:
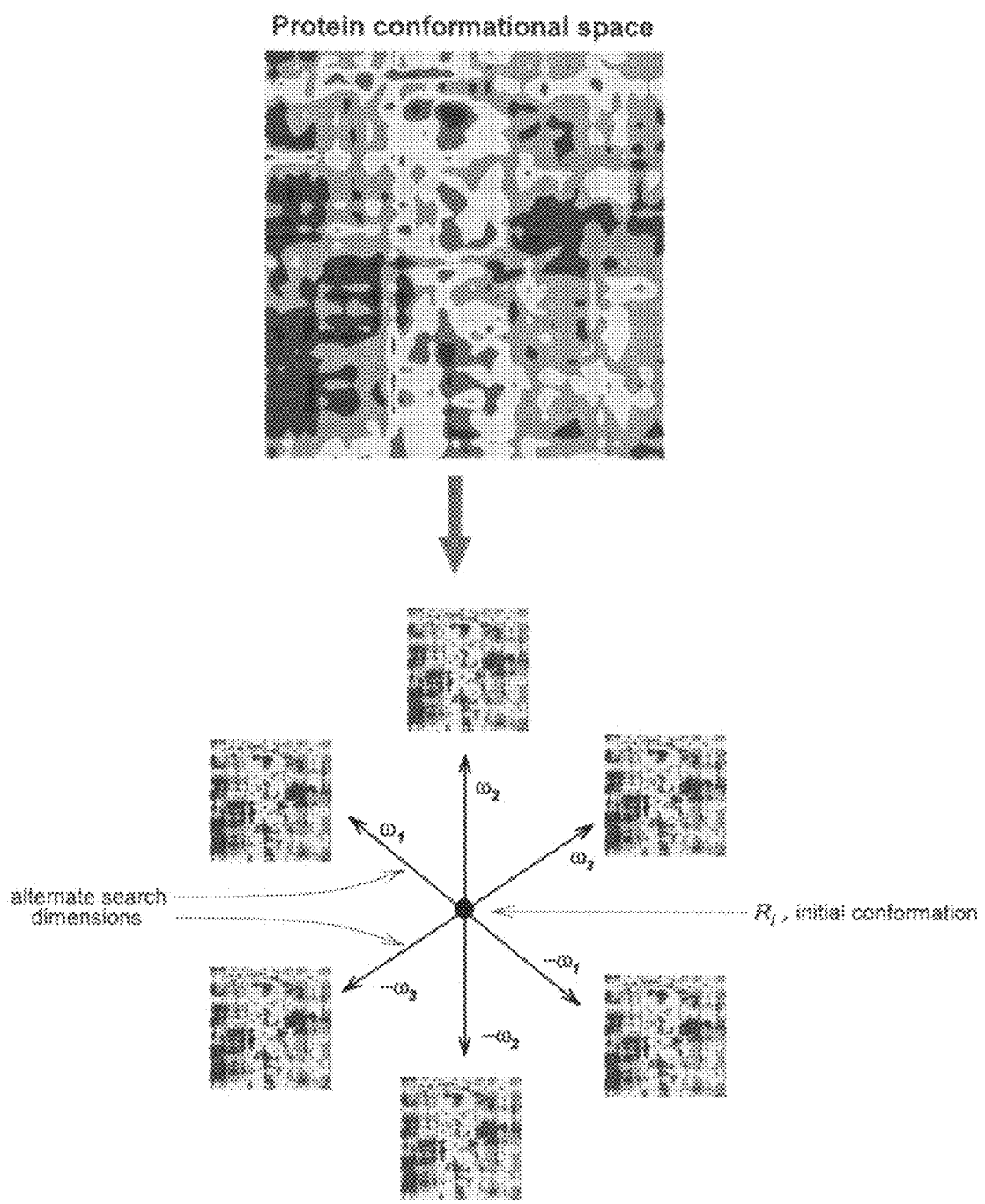
FIG. 2 is a schematic representation of the ability of the invention to reduce the complexity of a hypothetical protein conformational space by using a set of alternate search dimensions simultaneously.
Figure 4:
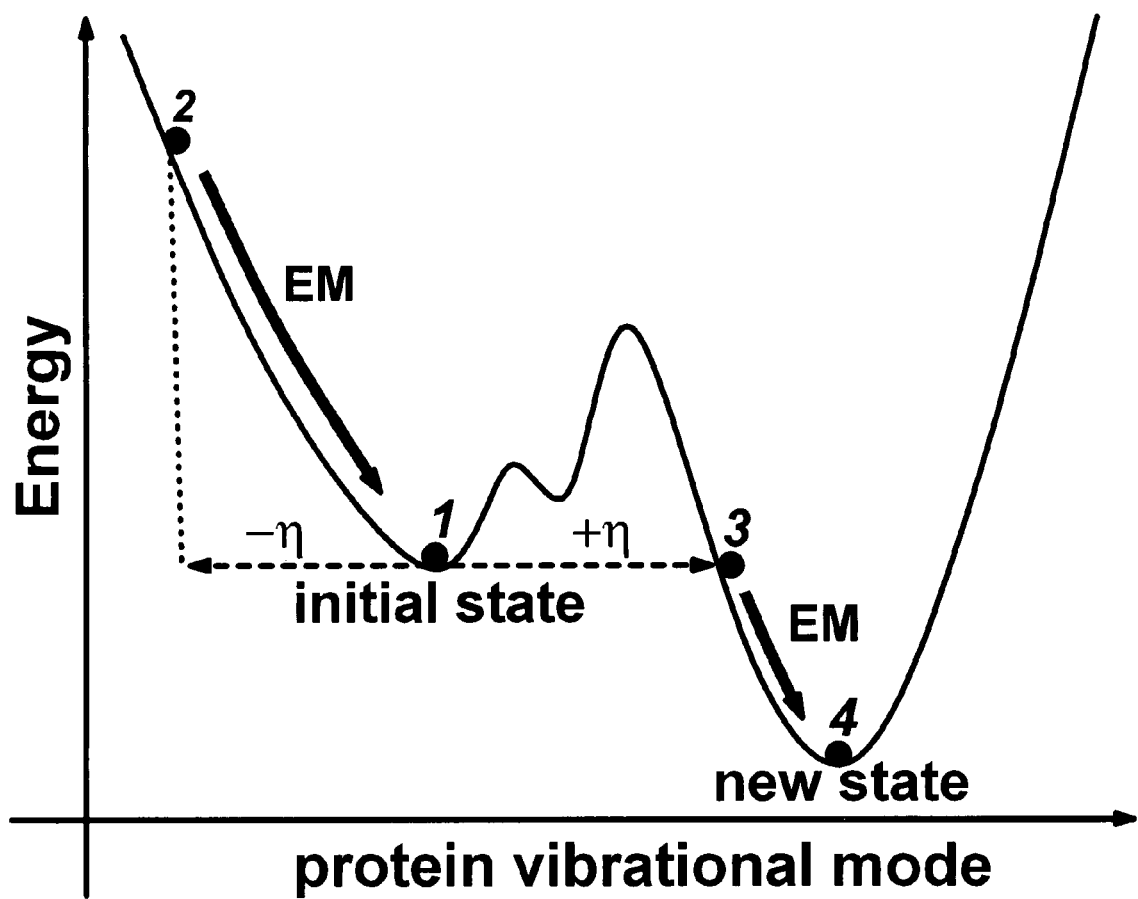
FIG. 4 is a schematic representation of the physical basis underlying the protein prediction method in one embodiment of the invention. State 1 is the initial protein conformation and it is displaced using the protein vibrational modes determined for that conformation in negative and positive directions (indicated by the dashed horizontal arrows and $-\eta/+\eta$). In this case the displaced protein conformation in state 2 is higher in energy and is returned to the initial conformation of state 1 upon energy minimization. The displacement of the conformation in the opposite direction (state 3), however, passes through a region with an energy barrier; and upon energy minimization leads to a new energy minimum and corresponding protein conformation (state 4).

The present method searches the protein conformational energy landscape by utilizing protein vibrational modes as the search dimension. Vibrational modes describe the atomic velocities and magnitudes of motion of each atom in the protein molecule. Using the Cartesian coordinates of an extended or partially folded protein conformation, the present method iterates through a series of energy minimization, molecular dynamics and calculation of the protein vibrational modes. There are several computational techniques that are available for the calculation of protein vibrational modes including the normal mode analysis, time-averaged normal coordinate analysis, Gaussian network model and quasi-harmonic analysis. In one embodiment of the present invention, the coordinates of the protein can then be displaced along these vibrational modes producing new protein conformations. The displaced conformation will either result in a higher energy state and return to the initial conformation upon energy minimization, or will pass through an energy barrier and result in a new energy minima upon energy minimization (FIG. 4). An important aspect of the present method is the ability to search the protein conformational energy landscape using multiple vibrational modes simultaneously in independent searches (corresponding to alternate pathways in the mechanism of protein folding), thereby greatly enhancing the speed at which the search is performed (FIG. 2). After displacing the initial conformation along select vibrational modes, the potential energies of the resulting displaced conformations are compared. The conformation with the lowest potential energy minima is then accepted as the new starting conformation and the process is repeated until the native conformation at the global minima is determined. The conformation at the local energy minimum also represents an intermediate in the protein folding pathway In an alternative embodiment, rather than displace the protein conformation along the vibrational modes, kinetic energy can be added to the protein vibrational mode by scaling the velocities proportional to the atomic displacements indicated by the protein vibrational mode. This increased kinetic energy will then allow the conformation to overcome energy barriers and proceed to the native fold. In one embodiment an increase of 5-25% of total system kinetic energy (protein+solvent) is added to each vibrational mode. In another embodiment all of the total system kinetic energy is added into a single vibrational mode. In yet another embodiment an increase of 0.01-5% of total system kinetic energy is added to each vibrational mode.

Implicit and Explicit Solvation Models

All proteins are surrounded by a solvent such as water or lipids or mixtures thereof (combination of solvents). The native structure and behavior of a protein is dependent on the properties of the surrounding medium. In explicit solvation methods the solvent is treated by representation of solvent with assignment of point masses and charges and these solvent molecules are modeled in the simulation (W. L. Jorgensen et al., J. Chem. Phys. 79, 926-935 (1983), W. L. Jorgensen et al., Mol. Phys. 56, 1381-1392 (1985)) However, such a description makes the calculations slower. Therefore an approximation has been designed that mimics bulk properties of the water by an empirical description of the electrostatic properties that impact the protein. These models are known as implicit solvation models (C. J. Cramer et al., Chem. Rev. (1999), 99, 2161-2200). The present method is equally suitable for use with both implicit and explicit solvation models Determining the Initial Protein Conformation The input for this method is an initial set of Cartesian coordinates available to one of ordinary skill in the art, for example in a protein database. While the method requires nothing more than the primary sequence of the protein to assign initial coordinates, these coordinates can be provided from other sources. For example, information about coordinates from experimental techniques including but not limited to nuclear magnetic resonance spectroscopy, X-ray crystallography, X-ray scattering, small angle neutron scattering, or multi-dimensional infrared spectroscopy can be used as the initial input. Alternatively, conformational information from other structural prediction programs such ROSETTA, ROBETTA, PROSPECT or other similar structure prediction programs can be used. If starting from the primary sequence any reasonable geometrical arrangement of the protein atoms can be used as an initial structure. However, the bond lengths and angles should not be far away from their equilibrium positions, to avoid numerical failures of the EM/MD program used. For example, a linear arrangement of main chain atoms with side chains perpendicular to the main chain is a valid starting configuration. Similarly the main chain can be arranged as a helix with the side-chains pointing away. Any other physically reasonable extended conformation, which does not stretch bonds or angles/dihedrals is equally acceptable. Computer programs such as AMBER (J. Computat. Chem. 26, 1668-1688, 2005), tLeap or xLeap modules provide a method (command "sequence") to prepare an extended conformation and Cartesian coordinates based on the primary sequence.

Energy Minimization

The goal of energy minimization is to find a local energy minimum for a potential energy function. A potential energy function is a mathematical equation that allows the potential energy of a molecular system to be calculated from its three-dimensional structure. Examples of energy minimization algorithms include, but are not limited to, steepest descent, conjugated gradients, Newton-Raphson, and Adopted Basis Newton-Raphson (Molecular Modeling: Principles and Applications, Author A. R. Leach, Pearson Education Limited/Prentice Hall (Essex, England), $2^{nd}$ Edition (2001) pages: 253-302). It is possible to use several methods interchangeably. For example, a lower order algorithm, such as steepest descent is used initially to provide a rough approximation of the energy minima. As the protein folding simulation progresses, a higher order algorithm such as Newton-Raphson is optionally used to provide a more accurate determination of the energy minima. Likewise, several algorithms are optionally used concurrently by combining them into a single energy minimization protocol. For example, a method such as steepest descent can be used to quickly approximate the minima, followed by a higher order algorithm, such as Newton-Raphson, to more accurately pinpoint the minima. As known in the art, higher order algorithms that use more information about a function are generally more accurate at the expense of being computationally more expensive. The determination of which algorithm or combination of algorithms to use can be determined by one of ordinary skill in the art based on his or her need to balance these two factors. Preferred methods are steepest decent for its speed and conjugate gradients for its ability to converge quickly.

Molecular Dynamics

Molecular dynamics simulations are used to monitor time-dependent processes in molecular systems in order to study their structural, dynamic, and thermodynamic properties by solving the equation of motion for a molecule. This equation of motion provides information about the time dependence and magnitude of fluctuations in both positions and velocities of a given molecule. The direct output of molecular dynamics simulations is a set of "snapshots" (coordinates and velocities) taken at equal time intervals, or sampling intervals. Depending on the desired level of accuracy, the equation of motion to be solved may be the classical (Newtonian) equation of motion, a stochastic equation of motion, a Brownian equation of motion, or even a combination (Becker et al. eds. Computational Biochemistry and Biophysics New York 2001). There are a number of ways to implement molecular dynamics simulations and examples of suitable simulation packages include, but are not limited to, CHARMM (J. Comp. Chem. 4, 187-217, 1983), AMBER (J. Computat. Chem. 26, 1668-1688, 2005), GROMACS (D. van der Spoel et al., J. Comp. Chem. 26 pp. 1701-1718 (2005), TINKER (J. W. Ponder et al., J. Comput. Chem., 8, 1016-1024 (1987)), NAMD (J. C. Phillips et al., J. Comput. Chem., 26:1781-1802, 2005) and LAMMPS (S. J. Plimpton, J. Comp. Phys., 117, 1-19 (1995).

The input coordinates for molecular dynamics for the present invention are based on the coordinates of the extended conformation for the first cycle and thereafter by the coordinates of the lowest energy conformation determined in the previous cycle. The time step can be varied between cycles. The time integration step is typically set to be smaller than the fastest degree of motion. In a preferred embodiment the time integration step is set to about 1 fs if the bonds involving hydrogen are not fixed and about 2 fs if the bonds involving hydrogen are fixed. The initial velocity distribution is determined by the temperature of the system and is usually assigned from the standard Maxwellian velocity distribution for a given temperature, T.

The sampling interval (that is the duration of the molecular dynamics trajectory) is determined according to the time scale of the protein motion to be sampled. For the present invention the sampling intervals that are relevant for providing the protein vibrational modes range from $10^{-15}$ seconds to 1 second (either in single trajectory or as a collection of trajectories). In another embodiment the sampling interval is about $10^{-15}$ seconds to about $10^{-6}$ seconds. In another embodiment the sampling interval is about $10^{-15}$ seconds to about $10^{-12}$ seconds. In yet another embodiment the sampling interval is about $10^{-12}$ seconds to about $10^{-6}$ seconds. The sampling interval can be varied from one cycle to the next. Longer sampling intervals allow computations of the slower vibrational modes, which have implications in overcoming larger energy barriers. Intermediate and faster vibrational modes have implications in overcoming smaller barriers. Table 1 summarizes the time scales of various motions to be sampled and their relevance in predicting the native fold of the protein. Initially, vibrational modes associated with slower time scales are used to rapidly sample large areas of the conformational space. As the conformation begins to converge towards the global minimum sampling the intermediate and fast time scales is used to further refine and converge the conformation to a local or global minimum.

TABLE 1

Summary of motions in proteins

| | Fast | Intermediate | Slow |
|---|---|---|---|
| Time-scale(s) | $10^{-15}$ to $10^{-12}$ s | $10^{-12}$-$10^{-6}$ s | >$10^{-6}$ s |
| Regions of proteins involved | Few atoms, single residue or side-chain atoms | Few amino acid residues, loop regions, alpha-helices and beta-sheets | Larger regions of proteins and even entire protein; single or multiple domains |
| Relevance for the present invention in protein folding | Convergence within the local or global energy minimum | Moving over the barriers separating the local energy minima and convergence toward the global energy minima | Large energy barriers that separate the distant areas of the protein conformational space. Gradual moves toward the global energy minimum. |

Computation of the Protein Vibrational Modes

Vibrational modes of a protein are modeled by a set of displacement vectors for each atom in the protein. Several methods are available to compute the vibrational modes of a molecular system such as a protein. A list of suitable methods for use with this invention to compute the protein vibrational modes are discussed below:

1. Normal mode analysis (NMA):

This method computes vibrational modes of a molecular system by diagonalization of the Hessian matrix (see Molecular Modeling: Principles and Applications, A. R. Leach, Pearson Education Limited/Prentice Hall (Essex, England), $2^{nd}$ Edition (2001) pages: 273-275). Assuming the molecular system has N atoms, the Hessian matrix is a 3N×3N matrix. The elements of the matrix are the second order energy derivatives with respect to the displacement of atomic positions in the x, y, z directions. The elements can be computed analytically or computationally. Once the Hessian matrix is computed, it is diagonalized to solve for the eigenvectors and eigenvalues.

$$\epsilon_i F = \epsilon_i \omega_i \quad \text{(Eq. 2)}$$

The time-scale of molecular vibration is determined by taking the inverse square root of the eigenvalues ($\epsilon$) obtained after diagonalization (Molecular Modeling: Principles and Applications, A. R. Leach, Pearson Education Limited/Prentice Hall (Essex, England), $2^{nd}$ Edition (2001) pages: 15-16). The eigenvector ($\omega$) corresponding to the eigenvalue represents the vibrational modes, which are a set of displacement vectors for the atoms in the molecular or the protein conformation.

2. Time-averaged normal coordinate analysis (TANCA):

This method is similar to NMA in the sense that the protein vibrational modes are obtained by diagonalization of the Hessian matrix (Hathorn B. C. et al., J. Chem. Phys. A., 106 (40): 9174-9180 Oct. 10, 2002, and Tuzun R. E. et al., Macromol. Theor. Simul. 11 (7): 711-728 Oct. 18, 2002)). However, NMA suffers from some limitation when considering a highly flexible molecular system such as a protein. NMA uses a reference structure and the eigenvalues and eigenvectors thus obtained are only relevant to the reference starting structure. The method therefore weights highly toward the high frequency motions and less toward the low frequency motions. Moreover the low frequency obtained using NMA are not reliable for molecular conformations that differ considerably from the reference structure for NMA. In protein folding mechanism the low frequency motions are more important as they are required for overcoming the high energy barriers.

Techniques such as TANCA can partially overcome this problem by diagonalization of the Hessian matrix which has been constructed numerically by averaging the elements over time. This allows the fast frequency motions to be removed by averaging and provides more accurate low frequency modes that are relevant for protein folding. More details about this method are available in the references mentioned in the last paragraph.

3. Quasi-harmonic analysis (QHA):

This method computes protein vibrational modes from a set of protein conformations that are sampled using either the molecular dynamics (or Monte-Carlo) type simulations. QHA is a powerful method in obtaining vibrational modes that are representative of longer time-scales or the low frequency vibrational, by utilizing the information from a set of structures which may be separated by a long time scale—or from different parts of the protein conformational space. The vibrational modes are obtained by diagonalization of the atomic fluctuation matrix. For a protein with N atoms, the atomic fluctuation matrix, F is a symmetric 3N×3N matrix with term $F_{\alpha\beta}$ defined as:

$$F_{\alpha\beta} = \langle m_\alpha^{1/2}(x_\alpha - \langle x_\alpha \rangle) m_\beta^{1/2}(x_\beta - \langle x_\beta \rangle) \rangle \quad \text{(Eq. 3)}$$

where $\alpha,\beta$ run through the 3N degrees of freedom in Cartesian space and $m_\alpha$ is the mass of atom corresponding to the $\alpha$th degree of freedom and $x_\alpha$ are the Cartesian coordinates of the atom corresponding to the $\alpha$th degree of freedom. Quantities in < > denote an average determined from molecular dynamics simulation. To obtain the eigenmodes (vibrational modes) diagonalization of the atomic fluctuation matrix is performed (see Eq. 2). The time-scale of protein vibration is determined by taking the inverse square root of the eigenvalues ($\epsilon$) obtained after diagonalization (Molecular Modeling: Principles and Applications, Author A. R. Leach, Pearson Education Limited/Prentice Hall (Essex, England), $2^{nd}$ Edition (2001) pages: 15-16). The eigenvector ($\omega$) corresponding to the eigenvalue represents the protein vibrational modes, which are a set of displacement vectors for the atoms in the protein confirmation. Note one of the benefits of QHA is that multiple MD trajectories can be combined to construct the atomic fluctuation matrix—thus allowing vibrational modes to be computed that represent conformational changes between different areas of the protein conformational space.

4. Gaussian network model (GNM):

This type of calculation uses coarse-grained normal mode analysis to obtain protein vibrational modes (Doruker P, et al., (2002) J. Comput. Chem. 23 (1):119-127 and Haliloglu T, et al., (1997). Phys. Rev. Lett. 79 (16):3090-3093). These calculations use a simple parameter harmonic potential for the particles in the system. The eigenmodes are obtained by the diagonalization of Kirchhoff's matrix, which is similar to Hessian matrix, but uses a reduced model of the protein and treats the protein motions as Gaussian type motions.

Irrespective of the type of method described above, for a protein with N atoms, there are 3N–6 protein vibrational modes. These modes describe a variety of motions within the protein (see Table 1). The modes with fast time-scales indicate repeated movements of atoms, or a small group of atoms that occur as many as a billion to trillion times per second. The intermediate time scales are associated with concerted movements of a group of protein residues. The intermediate timescales span several orders of magnitude and are associated with motions of loop regions, alpha helices and beta-sheets. The modes associated with the slowest time-scales are associated with the overall conformational fluctuations of a protein that involve major domain(s) or even the entire protein. The protein motions at different time-scales correspond to kinetic energy to allow overcoming of a variety of energy barriers encountered by the protein in the folding process. The fastest motions in the range of $10^{-15}$ seconds to $10^{-12}$ seconds, overcome small energy barriers. The intermediate motions in the range of $10^{-12}$ seconds to $10^{-6}$ seconds are important for overcoming medium height barriers. The slowest motions at scale of $10^{-6}$ seconds and slower (i.e. >$10^{-6}$ seconds) are important for overcoming large energy barriers. Therefore using vibrational modes associated with the slowest motions can find conformations within the conformational energy landscape that are separated by high energy barriers. Likewise the vibrational modes associated with the intermediate and faster motions are useful for inducing more local conformational changes, like the movement of a loop region, an alpha helix, or the side chains of individual residues. Accurate estimates of energy associated with the protein vibrational modes is currently not available, however, the lower estimations would correspond to energy associated with vibrations of individual bonds (<1 kcal/mol) and on the higher end correspond to movement of entire protein domains (5-10 kcal/mol or higher).

In the present invention the vibrational modes used are associated with time scales from about $10^{-15}$ seconds to about 1 second (computed from a single molecular dynamics trajectory or a collection of trajectories). In another embodiment the vibrational modes used are associated with time-scales in the range of $10^{-15}$ seconds to about $10^{-6}$ seconds. In another embodiment the vibrational modes used are associated with time-scales in the range of $10^{-15}$ seconds to about $10^{-12}$ seconds. In yet another embodiment the vibrational modes used are associated with time-scales in the range of $10^{-12}$ seconds to about $10^{-6}$ seconds. The number of vibrational modes that can be analyzed per cycle is limited only by the computational resources available. In one embodiment the conformational space is searched using at least 1-20 vibrational modes per cycle. In another embodiment the conformational space is searched using 20-50 vibrational modes per second. In another embodiment the conformational space is searched using 50-100 protein vibrational modes. In another embodiment the conformational space is searched using more than 100 protein vibrational modes. The number of vibrational modes used per cycle does not have to remain constant throughout the simulation and can be changed from cycle to cycle. When starting from the extended conformation the slower vibrational modes are important and therefore the first 10-20 modes associated with the slow motions are useful. Such a number can be repeated until the energy of the system ceases to decrease. In the case where exploring all these modes does not lead to decrease in energy then the number of modes is increased to 20-50. Similarly when these modes fail to produce additional decreases in energy the next 50-100 modes are investigated.

The evaluation criteria for the reaching the native state is based on evaluation of appropriate scoring functions and monitoring their progress as the 5 steps are repeated cyclically (FIG. 3). The basic assumption of reaching the native state is that global energy is at the minimum at this stage, therefore, no further decrease will be observed. It is observed that the energy of the system as well as the overall shape of the system starts to change quickly in the beginning cycles. However, when approaching the native state the energy convergence becomes slower and a smaller decrease in energy is observed between subsequent cycles. In one embodiment, all the protein vibrational modes are explored and if the energy does not decrease at all then the native state is reached. However, if the number of protein vibrational modes is very large, this approach may not be possible with some computing systems due to the large amount of computational time required. In another embodiment, a limited number of protein vibrational modes is tested, for example 500 to 1000 modes for large proteins, and if neither a significant decrease in potential energy (for example more than 1 kcal/mol) or a large change in structure with small change is energy is observed then the system is fairly close to the energy minimum.

In the beginning of the process, a limited number of vibrational modes are explored. To test for full convergence, about 3-25% of the modes are explored, depending upon the level of accuracy desired. It is to be understood that any percentage of the modes within the range of 3 to 25% may be explored. In situations where a lower degree of accuracy is acceptable, no more than about 3-10% of the vibrational modes are explored. In situations when high accuracy is desired then about 20-25% of the vibrational modes can be explored. Note that if a case occurs that a small change in energy in a subsequent cycle is encountered with a large change in structure, the current conformation may be in a local minima and the new conformation should be explored further by calculating the typical number of modes. Moreover protein vibrational modes constructed using QHA based on protein conformations from different parts of the conformational landscape facilitate jumping across barriers quickly. In the "folding funnel" concept (mentioned earlier), this equates to having reached the near global minima such that all modes lead to an increase in energy. As a general rule 3-25% of vibrational modes can be explored for convergence to the native state.

Predicting Protein Structure

In one embodiment, the method of the present invention comprises a cyclic exploration of the protein conformational space (FIG. 3). Each cycle comprises a combination of energy minimization, molecular dynamics directed by protein vibrational modes, and computation of the protein vibrational modes, displacing the system along the protein vibrational modes and then allowing the system to relax. First, an energy minimization is performed with an extended conformation then a molecular dynamics run is performed. The structures sampled during the molecular dynamics are used for quasi-harmonic analysis to obtain the protein vibrational modes. The QHA also provides an average conformation ($R_{avg}$). New areas of the protein conformational space are then searched based on these protein vibrational modes ($\omega$). For each vibrational mode ($\omega$), two searches are conducted (in the positive and negative displacement directions) generating two new conformations (Eq. 4 and Eq. 5) per vibrational mode analyzed.]

$$R_+ = R_{avg} + \eta \omega_i \quad \text{(Eq. 4)}$$

$$R_- = R_{avg} - \eta \omega_i \quad \text{(Eq. 5)}$$

Parameter $\eta$ indicates the magnitude of this displacement. Note that a large value of $\eta$ results in extremely high energy protein conformation with many overstretched bonds and close atom-atom interactions in $R_+$ or $R_-$, similar to the changes which occur when a large time step is taken in molecular dynamics simulations. For medium $\eta$ values, the unfavourable and repulsive interactions can quickly be removed by energy minimization. The values of $\eta$ range from 1.001-1000. In a preferred embodiment the values of $\eta$ range from 2-50. The values of $\eta$ do not have to remain constant and can be varied from one cycle to the next. Factors affecting the choice of $\eta$ include, but are not limited to, the robustness of the underlying molecular dynamics program to handle distorted bonds, the convergence behaviour of the protein structure towards the global minimum; i.e. large values are useful in the beginning when the structure is far away from the native structure and smaller values are better for refinements. A total of 2*L independent searches are performed per cycle, L=number of modes investigated. For example, if the three lowest frequencies are analyzed then six displaced conformations are produced ($R_{1+}$, $R_{2+}$, $R_{3+}$, $R_{1-}$, $R_{2-}$, $R_{3-}$). For each search, the displaced conformations are then minimized to explore new areas of the conformational space. At the end of these independent energy minimizations, a comparison is made and the conformation with the lowest energy is selected. Once the conformation with the lowest energy is selected the cycle is repeated. This conformation represents an intermediate in the protein folding pathway.

Figure 5:
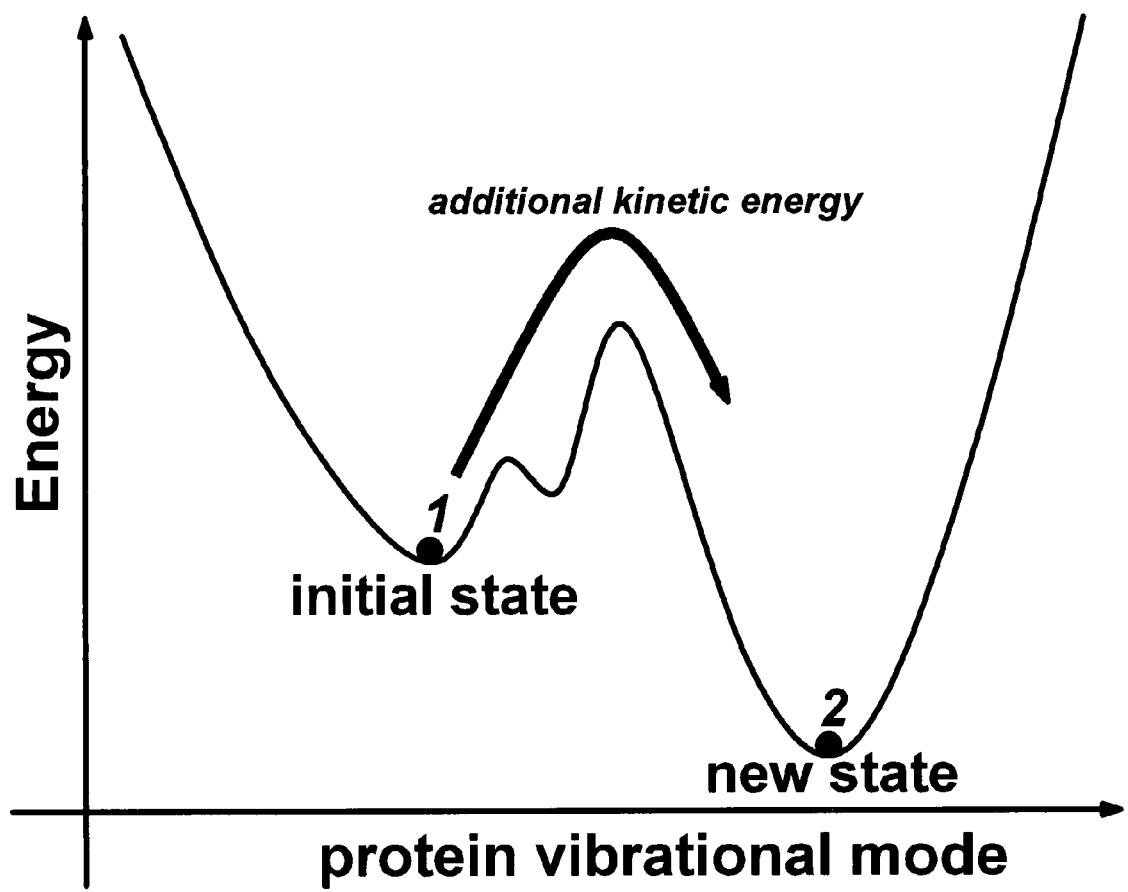
FIG. 5 is a schematic representation of an alternative embodiment of the present invention. In this method local energy barriers are overcome by addition of kinetic energy to protein vibrational modes. State 1 is the initial protein conformation. The addition of kinetic energy to the protein vibrational mode overcomes the barrier(s) along that mode to reach a new protein conformation (state 2).

In another embodiment, the local barriers in the energy landscape are overcome by adding energy to the protein vibrational modes. Like the previous embodiment an extended conformation is subjected to energy minimization followed by molecular dynamics and quasi-harmonic analysis to determine an average conformation ($R_{avg}$) and the vibrational modes of that conformation. However, rather than displace $R_{avg}$ along the vibrational modes, a different approach is used to add kinetic energy to the vibrational modes (FIG. 5). The amount of kinetic energy can vary over a wide range. In one embodiment 0.01% to 100% of the total system kinetic energy of the system is added to the vibrational modes. In another embodiment 0.01% to 5% of the total system kinetic energy of the system is added to the vibrational modes. In another embodiment 5% to 10% of the total kinetic energy of the system is added to the vibrational modes. In yet another embodiment 10% to 25% of the total kinetic energy of the system is added to the vibrational modes. In yet another embodiment 50%, 75% or 100% of the total kinetic energy of the system is added to a vibrational mode to overcome large energy barriers. It is to be understood that any amount of energy may be added provided it is sufficient to overcome energy barriers.

Kinetic energy is added to a protein vibrational mode by scaling the velocity proportional to the atomic displacements indicated by the protein vibrational mode. In the case of implicit solvent, this is simply done by multiplying the velocities by the factor (f). The values for this factor (f) range from 1 to 1000, with typical values of 2, 3, 4, 5, 6, 7, 8, 9, 10, 15, 20, 50 or any intermediate values.

In the case of explicit solvent, either a simple multiplication by factor (f) such as the one described above can be used, which results in an increase of the total system energy or the velocities of the system can be scaled to keep the total energy unchanged. The total system energy is kept unchanged by scaling down atomic velocities of the entire system (protein and solvent), according to the following equation:

$$\frac{1}{2}\sum_{i=1}^{N_{protein}}\sum_{\alpha} m_i[(1-\delta)^{1/2}v_{i\alpha} + \eta\varphi_{i\alpha}]^2 + \frac{1}{2}\sum_{i=1}^{N_{sol}}\sum_{\alpha} m_i(1-\delta)v_{i\alpha}^2 = \quad \text{(Eq. 6)}$$

-continued $$\frac{1}{2}\sum_{i=1}^{N_{total}}\sum_{\alpha} m_i v_{i\alpha}^2,$$

where v represents component of velocity for atom i; $m_i$ is the mass of atom, $N_{protein}$ is the number of solute atoms; $N_{sol}$ is the number of solvent atoms; $N_{total}$ are total atoms in the system; a represents summation over axes x, y, z; parameter δ represents the amount of energy transferred into the protein vibrational mode φ; and η is a variable calculated based on the above equation. Scaled velocities for atoms and solvent were assigned according to following expressions:

protein atoms: $v''_{i\alpha}=(1-\delta)^{1/2}v_{i\alpha}+\eta\phi_{i\alpha}$, (Eq. 7)

solvent: $v''_{i\alpha}=(1-\delta)^{1/2}v_{i\alpha}$. (Eq. 8)

The next step after the assignment of velocities is to propagate the system using MD. Note that the assignment of velocities gives a direction of movement of the atoms. Following the time-integration technique discussed above, the time-trajectories for the subsequent steps are generated. The assignment of velocities corresponds to the overall energy, therefore, the temperature of the system.

In both embodiments, progress towards the 3-dimensional fold of the native state is followed by evaluation of scoring functions. The most commonly used scoring functions include the energy of the system, surface area, radius of gyration and other properties. A number of scoring functions were used in the examples described below. These include monitoring the potential energy, total (potential+kinetic) energy, radius of gyration, solvent accessible area. The present invention does not depend on a particular scoring function. Moreover, as better scoring functions become available the present invention will provide better accuracies in the predictions of the protein structures.

The energy of the system is computed by evaluation of the potential function of the conformation during energy minimization and after molecular dynamics. Equation 1 is a typical function used to determine the potential energy of a protein conformation. The surface area calculation can be made using a number of available techniques including but not limited to MSMS and the NACCESS algorithm. As the protein progresses towards its native state, the system energy and surface area (polar and non-polar) show an overall decrease. When the energy of the system and surface area stabilize, or decrease by less than 1-2%, the protein has reached its native state. Additionally comparisons to partial structural information from experimental techniques such as NMR or X-ray crystallography can be made for proteins where such information is available. This would include comparing the hydrogen bonding, hydrophobic interactions and the secondary structure elements formed. The hydrogen bonding pattern includes formation of O—H . . . N and N—H . . . O type of hydrogen bonds between the main chains. The hydrophobic interactions include those interactions between non-polar interactions (particularly in the core of the protein). The secondary structural elements including α-helices, β-sheets and turns are considered to be present when a set of hydrogen bonds are formed between neighboring (spatially in the case of sheets) protein residues.

Determining Protein Mechanism of Folding

It has been shown experimentally that proteins contain nucleation points, regions within the primary structure where higher order structures initially form (Itzhaki L. S. et al., J. Mol. Biol. (1995)254(2):260-88.). It has also been shown that as little as a single amino acid residue within these nucleation regions can be critical to the foldability of the protein (Arai M. et al., J. Mol. Biol. (2003), 328(1):273-88). The ability to isolate the intermediate conformations in the folding pathway of a protein is crucial to identifying these nucleation regions and critical amino acid residues. However, these highly transient conformations may be difficult to isolate experimentally. Using the methods described above, the current invention determines the coordinates for all potential intermediates in a protein folding pathway. The nucleation regions are then determined by examining the intermediate conformations and identifying those intermediates where higher order structure initially forms. Once such a region is identified, information regarding the residues within the nucleation region and their contribution to the formation of higher order structure (loops, α-helices, β-strands/sheets) is determined. The current method provides information about the time scale of motion for amino acid residues. The amount of energy associated with the motion is indicative of the energy barrier the protein must overcome in order to reach that conformation. The current method also provides the coordinates of an amino acid residue in relation to neighboring amino acid residues. This information can be used to determine whether key interactions occur between residues such as, hydrogen bonding, disulfide bridges, or hydrophobic interactions are taking place. Furthermore, the method determines the sequence in which these events take place, thereby elucidating the key events that occur for a protein to reach its native state.

Refining Misfolded Structures

The invented technology can be used to refine and correctly fold previously misfolded protein structures. The starting conformational information can be obtained from a variety of computational or experimental techniques as discussed above. The 5 steps of FIG. 3 are iteratively repeated until the structure reaches the correctly folded state. Note, that the misfolded structure could be a result of trapping in a local minima separated by a large energy barrier. This could be overcome by using a large displacement along the vibrational mode or combination of vibrational modes, as well as addition of sufficient amount of kinetic energy in vibrational mode or a combination of the same.

Testing the Relative Stability of a Protein Structure

The relative stability of protein structure or a group of protein structure could also be tested with the invented technology. Starting from a protein conformation (including the native state), where the coordinates for the conformational are obtained from any computational or experimental techniques the five steps of FIG. 3 are repeated. The protein structure is considered relatively stable if it keeps returning to the starting conformation even after testing a large number of protein vibrational modes (either displacement along or addition of kinetic energy) with wide variety of η and factor f or percentage of kinetic energy as described above.

Computer Requirements

The present invention is preferably implemented in a computer environment. Computers in such an environment include a memory, which can be a computer-readable medium (CRM), such as a random access memory (RAM), coupled to a processor. The processor executes computer-executable program instructions stored in the client device, such as in the memory, as program code. Such processors may include a microprocessor, an ASIC, and state machines. Such processors include, or may be in communication with, media, for example computer-readable media, which stores instructions that, when executed by the processor, cause the processor to perform the methods described herein. Moreover, the processor can be any of a number of computer processors, such as processors from Intel Corporation of Santa Clara, Calif. and Motorola Corporation of Schaumburg, Ill. Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, switch, private or public network, or other transmission device or channel, both wired and wireless. The instructions may include code from any suitable computer-programming language, including, for example, C, C++, C#, Visual Basic, Java, Python, Perl, and JavaScript.

In general, the computer can be any type of processor-based platform that operates on any operating system capable of supporting one or more application programs. The may operate on any operating system capable of supporting an application, including Microsoft® Windows® or Linux. One embodiment of the present invention for real size proteins utilizes a parallel Linux type cluster with 200 or more nodes.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Thermostable Subdomain from Chicken Villin Headpiece

Figure 6:
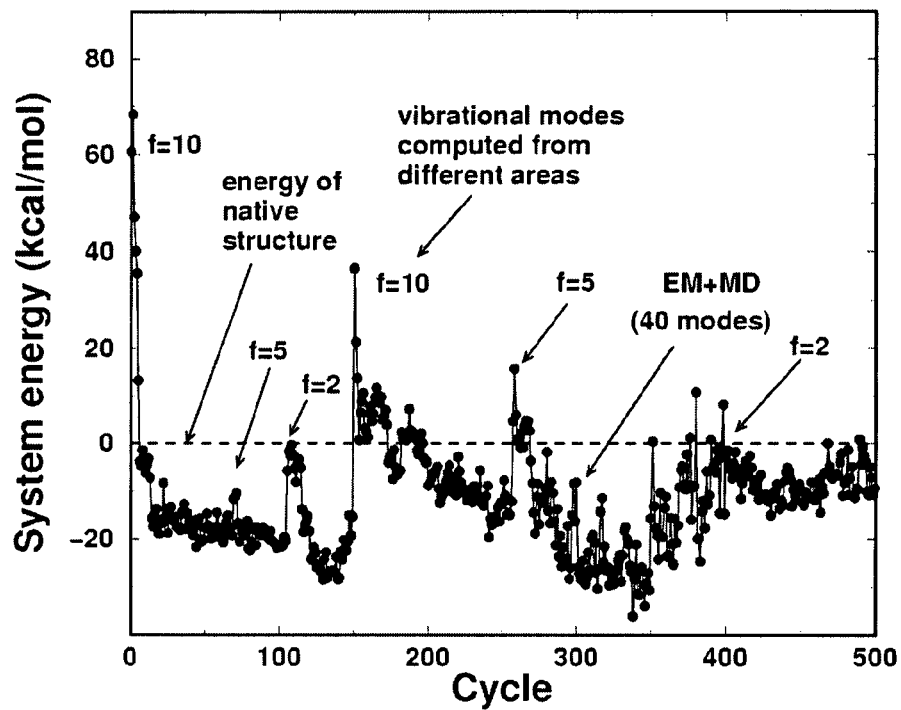
FIG. 6 is a schematic representation of (a) system energy and (b) non-polar surface area monitored during the protein folding process of chicken villin headpiece protein (Example 1). As expected, the total system energy showed a decrease. The various regions indicated by f=10, 5, 2 represent the proportional amount of kinetic energy added to the protein vibrational modes, where f=1 corresponds to the amount of naturally available kinetic energy in that mode. The energy of the native state is indicated by dashed horizontal line. Once during the run, to overcome slow convergence due to trapping in local minimum, the protein vibrational modes were computed from combining separate areas of the conformational space (Cycle 1-10 and 141-150), which allowed better convergence. Similarly at cycle 300, a slightly modified protocol was used for computing 40 modes per cycle and using the energy minimization as well as molecular dynamics for exploration of the relaxed structure after addition of kinetic energy. Note that in the last 100 steps, the energy did not decrease more than 1 kcal/mol, therefore, satisfying an energy based criterion for convergence. Similarly the non-polar surface area also satisfied a condition for convergence as it did not decrease more than 1% in the last 100 steps. Combining the two criteria, the lowest energy and lowest surface area, the native state was predicted around the cycles 398-400.
Figure 6:
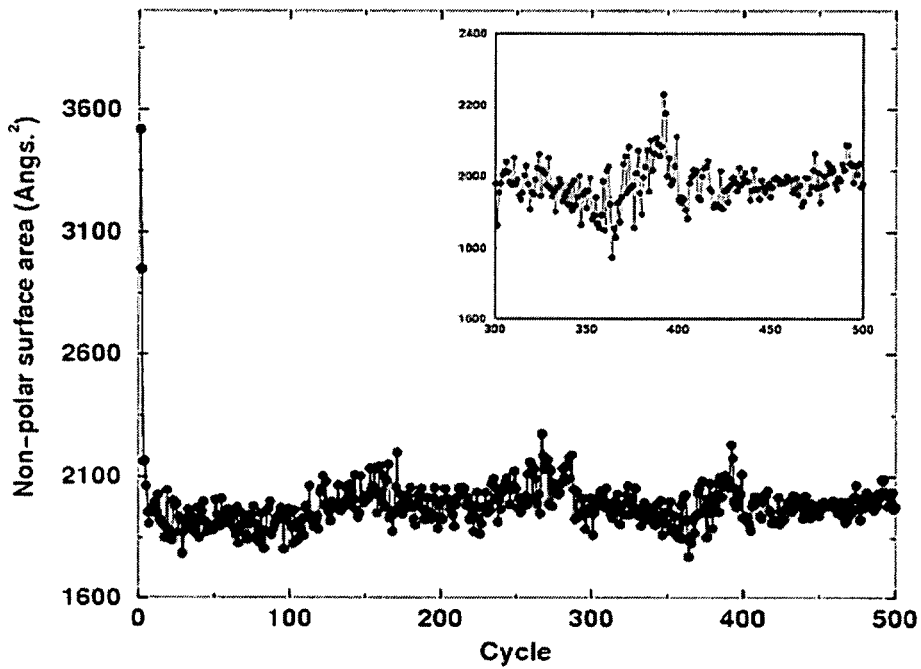
Figure 7:
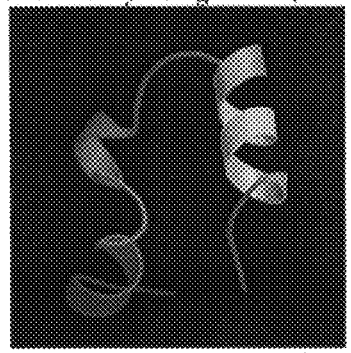
FIG. 7 is a schematic representation of selected structures determined during the process of folding the chicken villin headpiece protein (Example 1) using the instant invention. For comparison the experimentally (NMR) solved structure is shown in (a). This structure is available from the protein data bank (H. M. Berman et al., Announcing the Worldwide Protein Data Bank. (2003) Nature Structural Biol. 10 (12), p. 980) with the protein ID: 1 VII. The lowest panel (b) represents the results from the current invention. Shown in this panel are selected intermediates (at the end of listed cycles) during the mechanism of protein folding as represented by formation of the relevant secondary structure elements. Note that the secondary structure elements are shown in this and other examples as arrows (β-sheets) and coiled regions (α-helices). The formation of these secondary structures in the same places as the native structure is an important part of the protein folding process.
Figure 7:
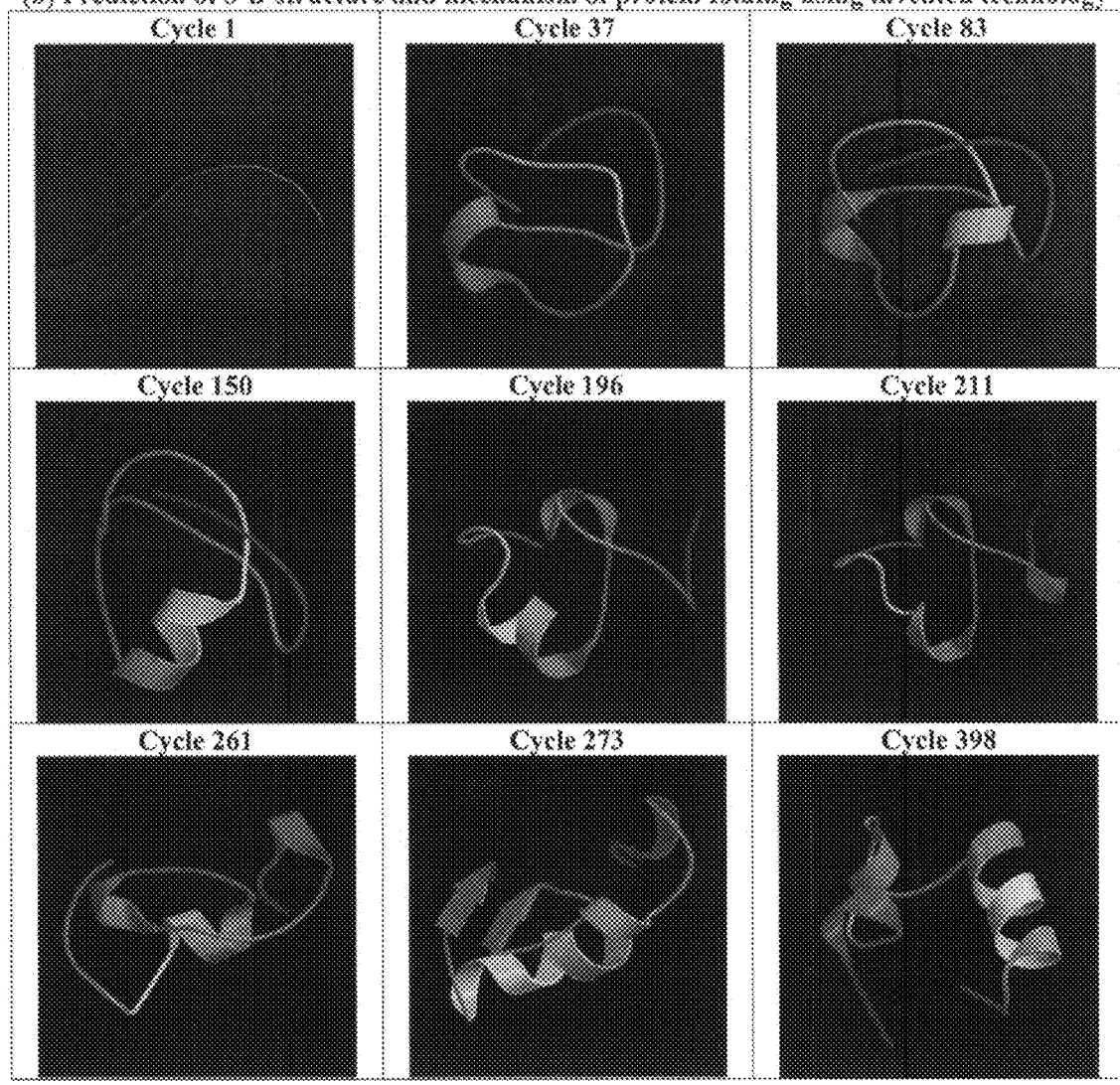

The present invention was used to determine the 3-dimensional structure as well as to investigate the mechanism of protein folding for the chicken villin headpiece protein. The chicken villin headpiece peptide is a 36-residue peptide, with known experimental structure solved using NMR (This structure is available from PDB code: 1VII). This analysis was performed by addition of kinetic energy to protein vibrational modes to overcome the energy barriers during the mechanism of protein folding. This was investigated using addition of kinetic energy to overcome the energy barriers during the mechanism of protein folding. For this example we used the implicit model description of the solvent (to accelerate the calculation). The calculations were performed using AMBER (J. Computat. Chem. 26, 1668-1688, 2005) force field (parm03) and the EM/MD engine sander (which is available as a part of AMBER package). More details about the force-field and EM/MD protocol are available in the above reference. These slowest modes are defined in Table 1 and are computed using quasi-harmonic, normal mode and/or TANCA type analysis. In this example, the vibrational modes were calculated using QHA. The extended conformation was prepared using "sequence" command in AMBER's tLeap module. Implicit solvent model (generalized Born method; V. Tsui et al., J. Am. Chem. Soc. 122, 2489-2498 (2000)) was used for these calculations as described in the AMBER documentation. The protein structure was subjected to the 5 stages of the present technology. At each mode, we evaluated 20 slowest modes and added kinetic energy. These slowest modes are defined in Table 1 and are computed using quasi-harmonic, normal mode and/or TANCA type analysis. After relaxation of the structure using a 10 nanosecond MD run, the structure with the lowest potential energy was selected as the starting structure for the subsequent step. The amount of kinetic energy added to the vibrational modes was determined by factor, f; f=1 corresponds to the naturally occurring kinetic energy in the mode. During this example f was changed from 10, 5 and 2 for better convergence. Moreover, to improve convergence once during the entire example the protein vibrational modes were calculated by using structures from different areas of the protein conformational space. This was performed by constructing the atomic fluctuation matrix using conformations from previous cycles. As different cycles sample different areas of the conformational space, the calculated modes were able to better structures. The results from this protein are shown in FIGS. 6-7.

The solved NMR structures show 3 helices present in the structure (helix 1: residues 4-8, helix 2: 15-18 and helix 3: residues 23-32). For a method for protein structure prediction and prediction of the protein folding mechanism, it is important that it predicts the 3 helices correctly and also shows the intermediates where these helices are being formed. The application of the present invention shows quick sampling of the conformational space to sample the formation of different regions very quickly. All the 3 helices are quickly sampled within the first 400 cycles, with helix 2 forming as early as cycle 37, and by cycle 150, helix 3 was being formed significantly. Moreover the progress toward the native like structure is shown by the formation of these secondary structural elements. Eventually the final structure closely resembles the native state with the presence of all 3 native helices (Cycle 398, FIG. 7*b*). Note, a general observation in this example is that the results show the structure is gradually improved as the cycles are performed. However as mentioned above, due to the force field effects, the energy quickly fell below the energy of the native protein. This example demonstrates that the present invention is able to predict the native structure elements correctly and moreover is able to provide information about the mechanism of protein folding.

EXAMPLE 2

The Native State of Ubiquitin

Figure 8:
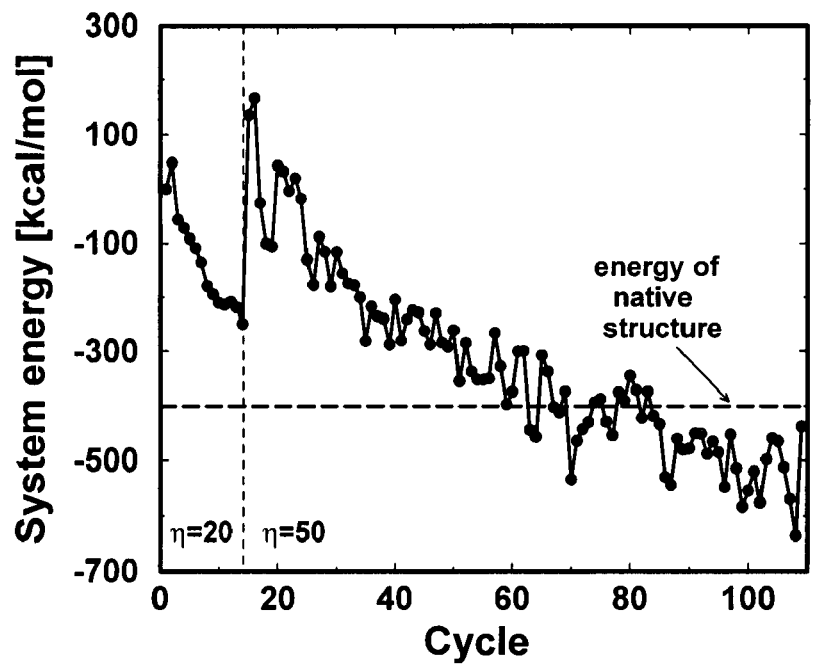
FIG. 8 is a schematic representation of parameters monitored during the protein folding process of Ubiquitin (Example 2). As expected, the total system energy (a) and total surface area (b) showed an overall decrease with increasing number of iterative cycles of the present invention.
Figure 8:
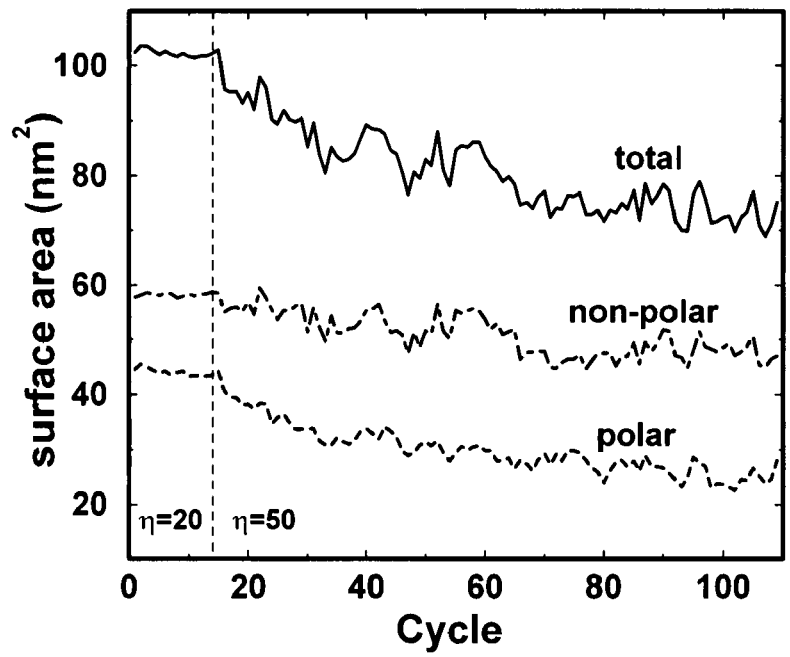
Figure 9:
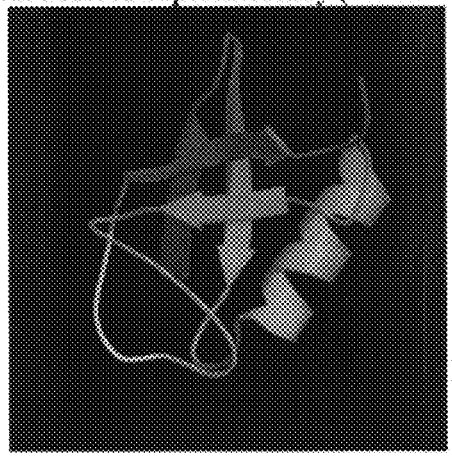
FIG. 9 is a schematic representation of selected structures determined during the process of folding the protein ubiquitin (Example 2) using the instant invention. For comparison the experimentally (X-ray diffraction) solved structure is shown in (a). This structure is available from the protein data bank (H. M. Berman et al., (2003): Announcing the Worldwide Protein Data Bank. Nature Structural Biology 10 (12), p. 980) with the protein ID: 1 UBQ. The results of the present analysis for the protein folding mechanism are shown in the panels (b) and (c). Intermediate structures at the end of listed cycles are shown. The middle panel (b) represents a test case using an explicit solvent. The lower panel (c) depicts results obtained with an implicit solvation model.
Figure 9:
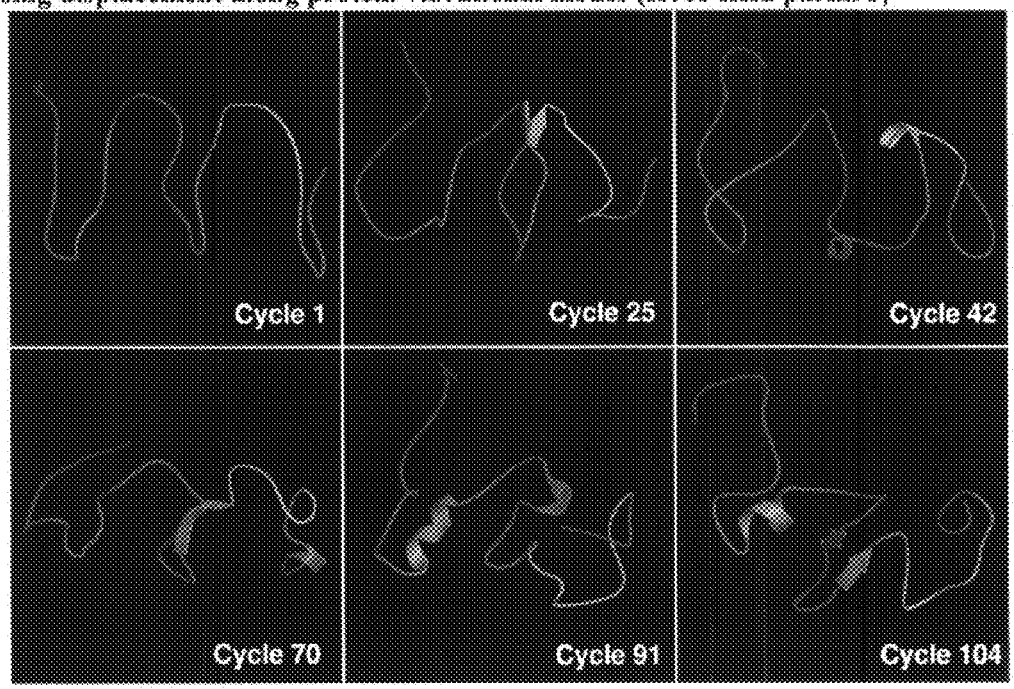
Figure 9:
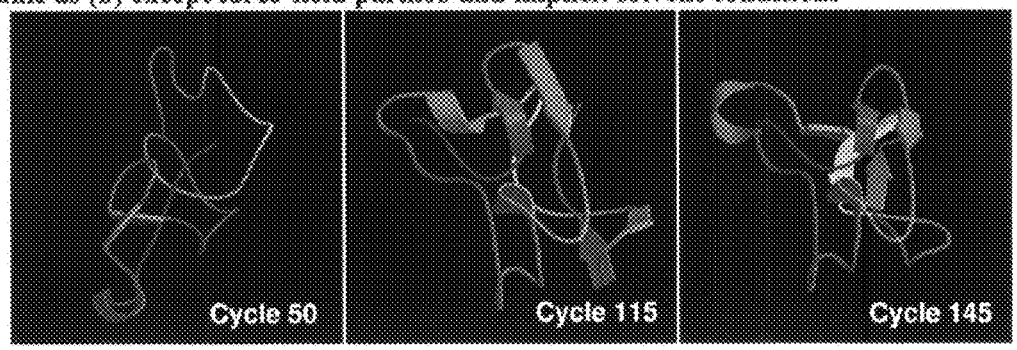

In this example the mechanism of protein folding for the protein ubiquitin was investigated and important protein regions were identified for the process of protein folding. Ubiquitin is a single chain protein composed of 76 amino acids and is a fully functional and naturally occurring protein present in living cell. Starting with a fully extended conformation in explicit solvent the ubiquitin structure was subjected to over 100 iterative cycles of the algorithm. As described in Example 1 above, AMBER package and force-field (parm 98) were used for setup, energy minimization and molecular dynamics runs. Note, this example used "displacement of protein structures along the vibrational mode" during stage 3. FIG. 8 depicts the variation of system energy and surface area as a function of the cycles and FIG. 9(*b*) depicts ubiquitin secondary structure at the end of selected cycles. A value of $\eta=20$ was used during the first 14 cycles, where a steady decrease in the system energy was observed. However, there was little change in the structure. An increased value of $\eta=50$ was therefore used beginning at the $15^{th}$ cycle. Secondary structural elements began appearing as early as the $15^{th}$ cycle. An α-helical formation appeared in the region 57-60, close to the native α-helix in the 56-59 region of the native protein. In the next few cycles this formation disappeared. A β-sheet formation, which was not present in the X-ray structure, appeared between residues 32-34 and 52-54 in the $25^{th}$ cycle. In this test case the selected value of η allows the present method to explore distant areas of protein conformational space very quickly, as indicated by regular formation and disappearance of secondary structure after the 30$^{th}$ cycle. Several turns, short α-helices and short β-strands were observed; some of these formations are present in the native structure. Almost all of the secondary structural elements in the native structure were observed to be present in different cycles. Several pieces of the native α-helix 23-34 region were observed after the 80$^{th}$ cycle. Fragments of the native β-sheets 40-45, 48-50, 64-72 regions were observed after the 45$^{th}$ cycle.

The total system energy and surface area (non-polar and polar) showed an overall decrease with increasing number of cycles, even though some cycles increased these quantities locally. The decrease in the system energy indicated the progress of the conformational search towards the global minimum. Decreases in polar and total surface area of the protein were consistent with the understanding of protein folding processes. A comparison was made with the known three-dimensional structure of ubiquitin. The current method predicted key structural elements (loops, α-helices and β-strands/sheets) found in the known structure. Likewise the surface area and system energy of the fold predicted by the current method were comparable to that of the known structure. A significant advantage of the present invention is the prediction of the mechanism of protein folding. The short native-like and non native secondary structural elements observed during these protein folding simulations are consistent with the experimental observations. A group of scientists used NMR experiments to observe the cooperative assembly of the ubiquitin fragment (M. Jourdan et al., Biochemistry, 39 (2000) 12355-12364.), and suggested that the formation of the helical core between resides 21-35 is an important nucleation event in protein folding. The present invention also indicated nucleation of this helical region in the early stages of the folding simulations and pieces of this helix were seen forming consistently in the example.

EXAMPLE 3

Dihydrofolate Reductase

Dihydrofolate reductase is a fully functional protein which functions as an enzyme. This protein is the target of anti-malarial and anti-cancer drugs. The power of the present invention is fully demonstrable in this example. This protein has more than 100 amino acid residues The sequence of dihydrofolate reductase from the bacterium *Escherichia coli* has 159 residues. The present technology was used to start from an extended conformation, in combination with implicit solvent model for water (generalized Born method). The preparation was similar to Example 1, where AMBER force-field (parm03) and package was used to prepare an extended conformation. The protein structure was subjected to 92 cycles of the present technology. Each cycle consisted of 10 picoseconds MD at stage 1; 5 picoseconds MD at stage 2; and 20 simultaneous searches using 10 vibrational modes (in positive/negative directions) with 10 picoseconds MD at stage 5.

Figure 10:
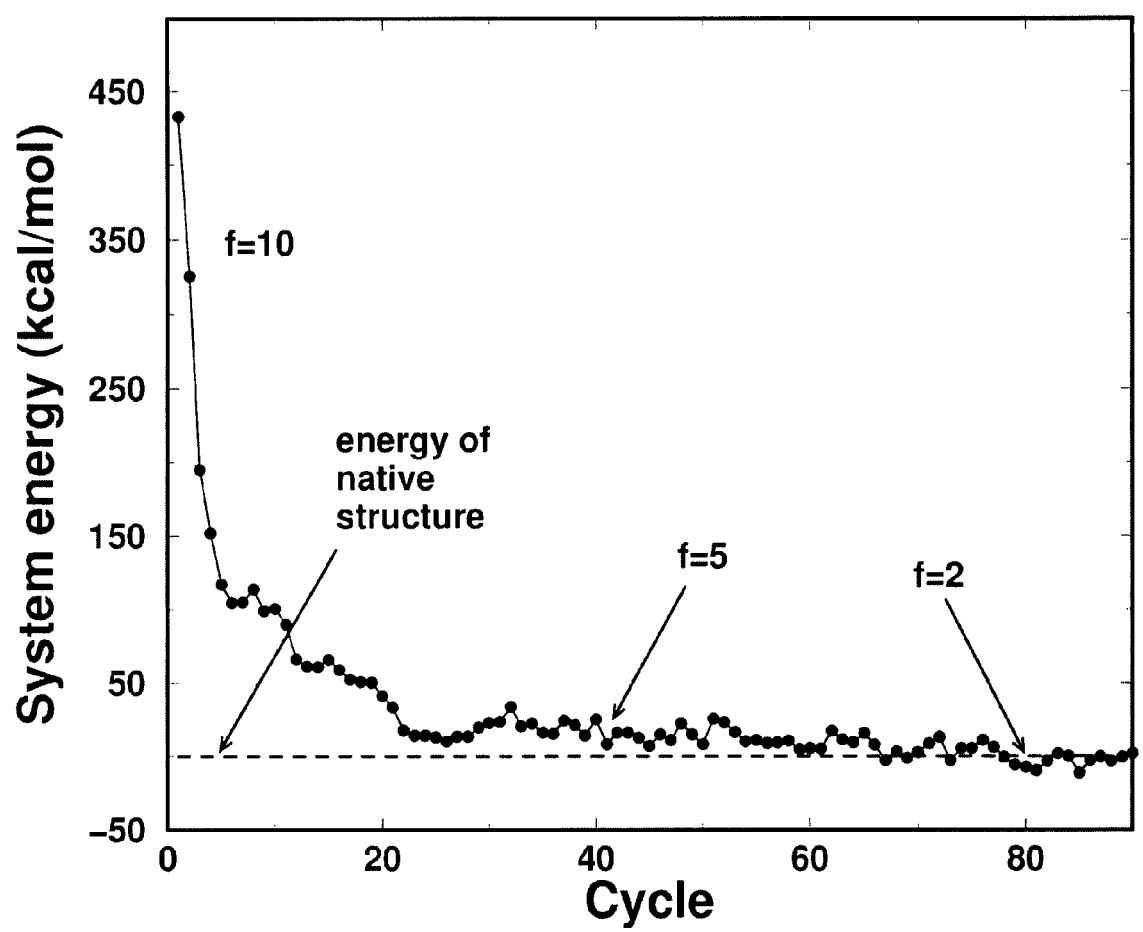
FIG. 10 is a schematic representation of parameters monitored during the protein folding process of dihydrofolate reductase (Example 3). As expected, the total system energy decreased with increasing number of iterative cycles of the present invention. The various regions indicated by f=10, 5, 2 represent the amount of kinetic energy added to the protein vibrational modes. The energy of the native state is indicated by dashed horizontal line.
Figure 11:
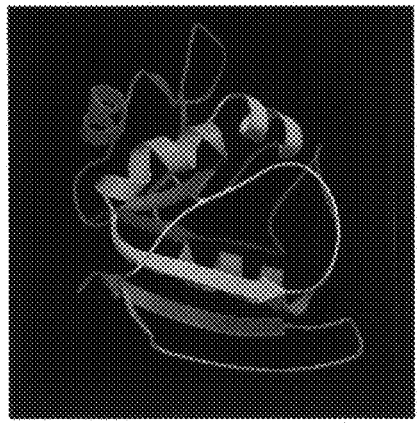
FIG. 11 is a schematic representation of selected structures determined during the process of folding *Escherichia coli* dihydrofolate reductase (Example 3) using the instant invention. For comparison the experimentally (X-ray diffraction) solved structure is shown in (a). This structure is available from the protein data bank (H. M. Berman et al., (2003): Announcing the Worldwide Protein Data Bank. Nature Structural Biology 10 (12), p. 980) with the protein ID: 1 RX2. The lowest panel (b) represents the mechanism of protein folding as represented by formation of the relevant secondary structure elements using the invented technology. Intermediate structures at the end of listed cycles are shown.
Figure 11:
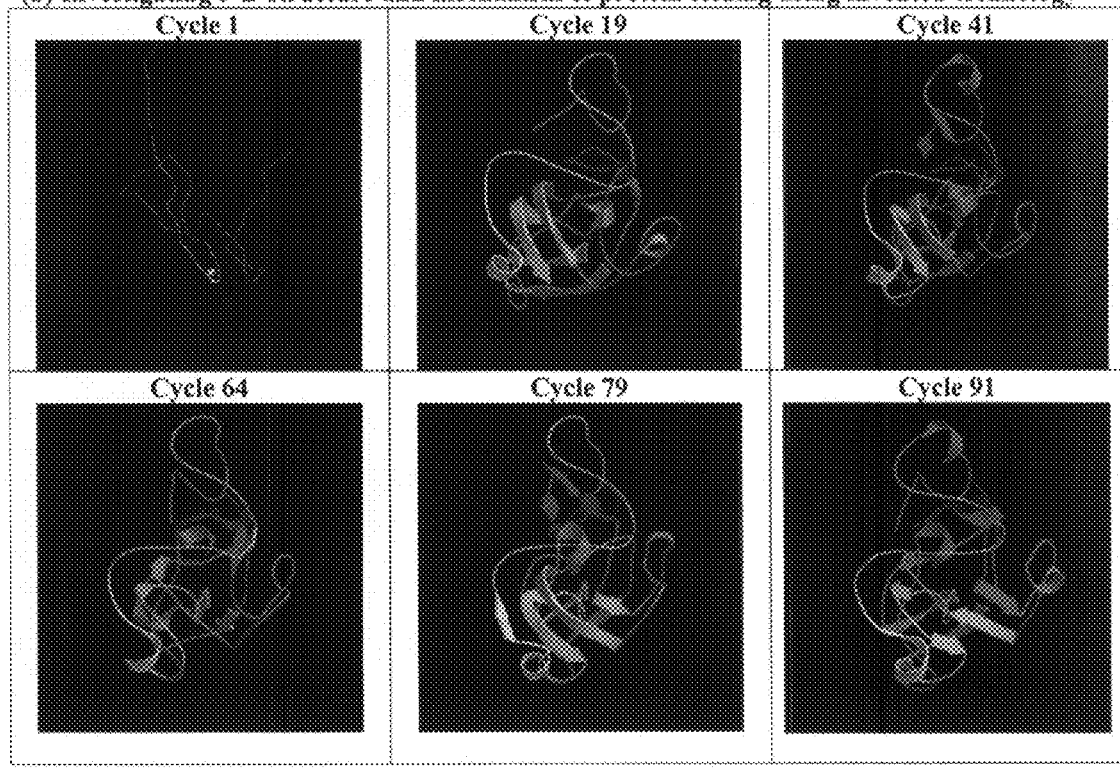

As indicated in FIGS. 10 and 11, the various secondary structural elements are quickly being sampled and they occur in different parts of the protein conformational space. Similar to Examples 1 and 2, the native secondary structure elements are shown in FIG. 11($a$) and are color coded (arrows indicate β-sheets and ribbons/coiled regions indicate native helices). From one cycle to another, the present invention quickly sampled distant areas of the conformational space, with the system energy quickly decreasing. As shown in FIG. 11($b$) the same and similar helices and beta-sheets quickly form as early as cycle 19 and continue to form until the end of cycle 91. We noticed that the energy quickly fell below the energy of the native structure—indicating a problem with the scoring function and leading to convergence difficulties. As mentioned above, the native energy of the protein is lowest, so being able to find non-native structures is an artefact of the problematic scoring functions. Nonetheless, this example illustrates that the present invention rapidly searched distant areas of the protein conformational space, moved from one local energy minima to another with overall system energy decreasing, quickly sampled the secondary structures present in the native structure and permitted prediction of the mechanism of protein folding. The system energy quickly approached a converged value. Once improved scoring functions are available, the present invention allows a highly accurate, if not precise, prediction of the protein structure.

In this example, the structure was subjected to only 25 picoseconds of MD trajectory per cycle (10 picoseconds for stage 1, 5 picoseconds for stage 2 and 10 picoseconds for stage 5; stage 3 and 4 do not need any MD or minimization), therefore, 92 cycles only correspond to 2300 picoseconds (2.3 nanoseconds) of molecular dynamics for the shown structure. The computing time required for the present invention (from start of cycle 1 to end of cycle 92) is almost the same as performing 2.3 nanoseconds of simple molecular dynamics trajectory. Note that stage 3 and 4 only take 2-3% of computing time. However, even in this short time-scale the native secondary structure elements (α-helices and β-sheets) are quickly discovered. It would typically take a protein more than 1 microsecond to form these structures in a simple molecular dynamics trajectory analysis of in vivo results. Therefore the present invention leads to more than a 500 fold increase in the speed of the search for native structure. Such speed is made possible by multiple and simultaneous searches of the conformational space at stage 5 and use of protein vibrational modes.

EXAMPLE 4

Cyclophilin A

Figure 12:
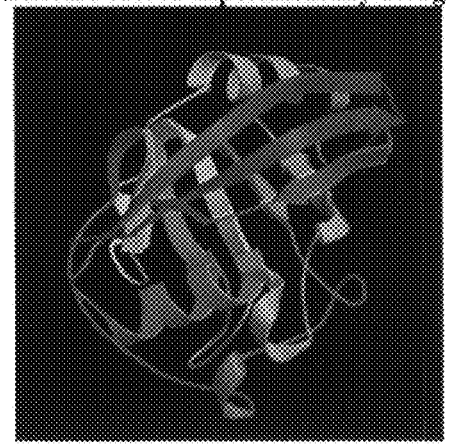
FIG. 12 is a schematic representation of selected structures determined during the process of folding human cyclophilin A (Example 4) using the instant invention. For comparison the experimentally (X-ray diffraction) solved structure is shown in (a). This structure is available from the protein data bank (H. M. Berman, et al., (2003): Announcing the worldwide Protein Data Bank. Nature Structural Biology 10 (12), p. 980) with the protein ID: 1 RMH. The lowest panel (b) represents the mechanism of protein folding as represented by formation of the relevant secondary structure elements using the invented technology. Intermediate structures at the end of listed cycles are shown.
Figure 12:
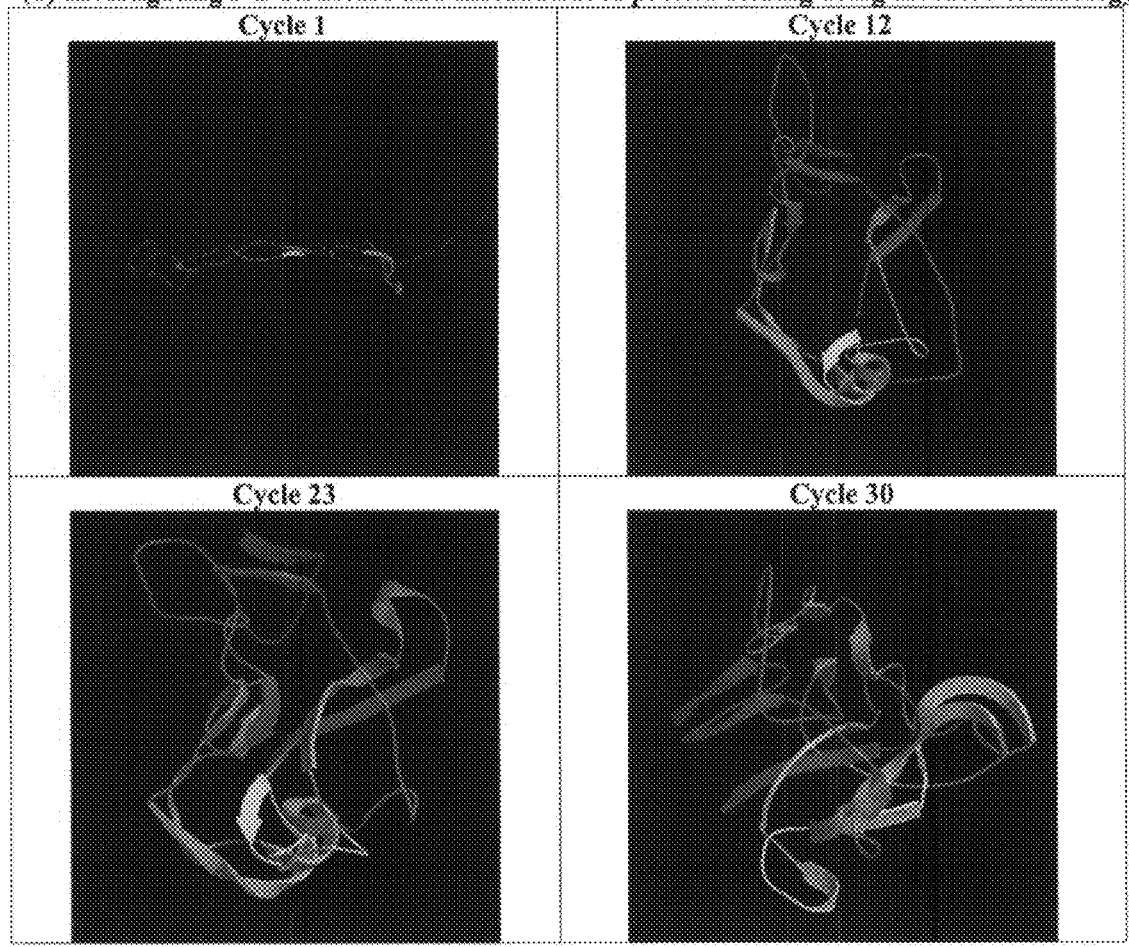

This is another example of a functional protein. In humans, this protein has 165 amino acid residues and plays a role in A peptidyl-prolyl cis/trans isomerization reaction, intracellular transport and also has a role in HIV-1 infection. The present technology was used in a similar way to example 3, however, we used energy minimization to relax the structures as compared to MD runs and 10 modes per cycle. Similar to Examples 1-3, the native secondary structure elements are shown in FIG. 12($a$) and are color coded (arrows indicate β-sheets and ribbons/coiled regions indicate native helices). The present invention quickly started to sample relevant areas of the conformational space, as shown in FIG. 12. The technology allows detailed investigations of the mechanism of protein folding. Several native β-sheets and α-helices start to form quickly during the conformational sampling process. The suitability of these secondary structure elements in the overall protein structure at the native state is inspected during the course of mechanism of protein folding. In this example, per cycle, the structure was subjected to only 15 picoseconds of MD trajectory plus 10,000 steps of energy minimization (10 picoseconds for stage 1, 5 picoseconds for stage 2 and 10,000 steps minimization for stage 5, stage 3 and 4 do not need any MD or minimization), therefore, 30 cycles only equal 750 picoseconds (less than 1 nanosecond) of molecular dynamics for the shown structure. The wall-clock time required for the present invention (from start of cycle 1 to end of cycle 30) is the same as performing 0.75 nanosecond of simple molecular dynamics trajectory. Note that stage 3 and 4 only take 2-3% of computing time. However, even in this short time-scale, the native secondary structure elements (α-helices and β-sheets) were quickly discovered. It would typically take a protein 1 microsecond or more to form these structures in a simple molecular dynamics trajectory (representing the case in vivo). Therefore the present invention leads to a more than 1000 fold increase in the speed of the search for native structure. Such speed is made possible by multiple and simultaneous searches of the conformational space at stage 5 and use of protein vibrational modes.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims

I claim:

1. A computer-based method for generating a model for a protein structure from a primary amino acid sequence of a protein comprising:
   providing a computer including a memory that is coupled to a processor, wherein said computer is configured to execute computer-executable program instructions including the steps of:
   a) defining an extended conformation from the primary amino acid sequence of the protein;
   b) relaxing the extended conformation;
   c) performing conformational sampling through molecular dynamics simulation on the relaxed extended conformation;
   d) computing an average structure ($R_{avg}$) and protein vibrational modes ($\omega$) based on the conformations sampled in step (c);
   e) determining two new protein conformations, $R_+$ and $R_-$, for each protein vibrational mode by displacing $R_{avg}$ along $\omega$ by a factor of $\eta$ in positive and negative displacement directions respectively;
   f) searching for local energy minima by performing energy minimization on $R_+$ and $R_-$ and selecting each new conformation with lowest energy;
   g) repeating steps (c) through (f) one or more times to produce one or more low energy conformations;
   h) selecting the lowest energy conformation structure from step (g);
   i) after performing step (h), performing conformational sampling through molecular dynamics simulation on a latest selected lowest energy conformation;
   j) computing an average structure ($R_{avg}$) and protein vibrational modes ($\omega$) based on the conformations sampled in step (i);
   k) adding kinetic energy to a protein vibrational mode ($\omega$) by scaling atomic velocities by a multiplication factor of f having a value selected from a range from 1 to 1,000 to produce a new configuration, wherein said atomic velocities are scaled in proportion to atomic displacements indicated by said protein vibration mode ($\omega$) by multiplying said multiplication factor off to each of said atomic velocities;
   l) searching for local energy minima by performing a molecular dynamics simulation on the new configuration determined in (k) and selecting a configuration with lowest energy among configurations generated by said molecular dynamics simulation;
   m) optionally repeating steps (i) through (l) for one or more times;
   n) repeating steps (c) through (m) until a native state of the protein is determined; and
   o) generating a molecular model of the protein at said native state;
   causing said computer to generate said molecular model by providing the primary amino acid sequence of the protein to said computer; and
   outputting, in a non-transitory tangible medium, a manifestation of said molecular model generated by said computer in a form capable of direct human perception.

2. A computer-based method for predicting a protein structure from a primary amino acid sequence of the protein comprising:
   a) defining an extended conformation from the primary amino acid sequence of the protein;
   b) relaxing the extended conformation;
   c) performing conformational sampling through molecular dynamics simulation on the relaxed extended conformation;
   d) computing an average structure ($R_{avg}$) and protein vibrational modes ($\omega$) based on the conformations sampled in step (c);
   e) adding kinetic energy to a protein vibrational mode ($\omega$) by scaling atomic velocities by a multiplication factor off having a value selected from a range from 1 to 1,000 to produce a new configuration, wherein said atomic velocities are scaled in proportion to atomic displacements indicated by said protein vibration mode ($\omega$) by multiplying said multiplication factor of f to each of said atomic velocities;
   f) searching for local energy minima by performing a molecular dynamics simulation on the new configuration determined in (e) and selecting the new configuration with lowest energy; and,
   g) repeating steps (c) through (f) until a native state of the protein is determined.

3. The method of claim 1, wherein relaxing the extended conformation is performed using energy minimization, molecular dynamics simulation or a combination thereof.

4. The method of claim 2, wherein relaxing the extended conformation is performed using energy minimization, molecular dynamics simulation or a combination thereof.

5. The method of claim 1, wherein searching for local energy minima in step f or step 1 further comprises energy minimization.

6. The method of claim 2, wherein searching for local energy minima in step f further comprises energy minimization.

7. The method of claim 1, wherein displacing $R_{avg}$ is performed using a combination of protein vibrational modes.

8. The method of claim 2, wherein in step e, kinetic energy is added to a combination of protein vibrational modes.

9. A computer-readable medium on which is encoded executable program code for predicting a protein structure from a primary amino acid sequence of the protein, the program code comprising the steps of:
   a) defining an extended conformation from the primary amino acid sequence of the protein;
   b) relaxing the extended conformation;
   c) performing conformational sampling through molecular dynamics simulation on the relaxed extended conformation;
   d) computing an average structure ($R_{avg}$) and protein vibrational modes ($\omega$) based on the conformations sampled in step (c);

e) determining two new protein conformations, $R_+$ and $R_-$, for each protein vibrational mode by displacing $R_{avg}$ along $\omega$ by a factor of $\eta$ in positive and negative displacement directions respectively;

f) searching for local energy minima by performing energy minimization on $R_+$ and $R_-$ and selecting each new conformation with lowest energy;

g) repeating steps (c) through (f) until one or more times to produce one or more low energy conformations;

h) selecting the lowest energy conformation from step (g);

i) after performing step (h), performing conformational sampling through molecular dynamics simulation on a latest selected lowest energy conformation;

j) computing an average structure ($R_{avg}$) and protein vibrational modes ($\omega$) based on the conformations sampled in step (i);

k) adding kinetic energy to a protein vibrational mode ($\omega$) by scaling atomic velocities by a multiplication factor off having a value selected from a range from 1 to 1,000 to produce a new configuration, wherein said atomic velocities are scaled in proportion to atomic displacements indicated by said protein vibration mode ($\omega$) by multiplying said multiplication factor off to each of said atomic velocities;

l) searching for local energy minima by performing a molecular dynamics simulation on the new configuration determined in (k) and selecting a configuration with lowest energy among configurations generated by said molecular dynamics simulation;

m) optionally repeating steps (i) through (l) for one or more times;

n) repeating steps (c) through (m) until a native state of the protein is determined; and o) generating a molecular model of the protein at said native state.

10. A computer-readable medium on which is encoded executable program code for predicting a protein structure from a primary amino acid sequence of the protein, the program code comprising: program code for
a) obtaining starting conformational information about the partially folded state of the protein from a structural prediction program or experimental source;
b) relaxing the extended conformation;
c) performing conformational sampling through molecular dynamics simulation on the relaxed extended conformation;
d) computing an average structure ($R_{avg}$) and protein vibrational modes ($\omega$) based on the conformations sampled in step (c);
e) adding kinetic energy to a protein vibrational mode ($\omega$) by scaling atomic velocities by a multiplication factor off having a value selected from a range from 1 to 1,000 to produce a new configuration, wherein said atomic velocities are scaled in proportion to atomic displacements indicated by said protein vibration mode ($\omega$) by multiplying said multiplication factor off to each of said atomic velocities;
f) searching for local energy minima by performing a molecular dynamics simulation on the new configuration determined in (e) and selecting the new configuration with lowest energy; and, g) repeating steps (c) through (f) until a native state of the protein is determined.

11. The method of claim 1, further comprising adding additional kinetic energy to at least another protein vibrational mode between step k and step l.

12. The method of claim 1, wherein said kinetic energy is added to said protein vibrational mode by scaling said atomic velocities proportional to atomic displacements indicated by said protein vibrational mode.

13. The method of claim 1, wherein a magnitude of said kinetic energy is greater than energy associated with vibrations of individual bonds and is less than energy corresponding to movement of an entire protein domain.

14. The computer-readable medium of claim 9, wherein the program code is configured to perform the step of relaxing the extended conformation by using energy minimization, molecular dynamics simulation or a combination thereof.

15. The computer-readable medium of claim 9, wherein the program code is configured to perform the step of searching for local energy minima in step f or step l through energy minimization.

16. The computer-readable medium of claim 9, wherein the program code is configured to perform the step of displacing $R_{avg}$ by using a combination of protein vibrational modes.

17. The computer-readable medium of claim 9, wherein the program code further comprises the step of adding additional kinetic energy to at least another protein vibrational mode between step k and step l.

18. The computer-readable medium of claim 9, wherein the program code is configured to perform the step of adding said kinetic energy to said protein vibrational mode by scaling said atomic velocities proportional to atomic displacements indicated by said protein vibrational mode.

19. The computer-readable medium of claim 9, wherein the program code is configured to provide a magnitude of said kinetic energy that is greater than energy associated with vibrations of individual bonds and is less than energy corresponding to movement of an entire protein domain.

* * * * *